(12) United States Patent
Liu et al.

(10) Patent No.: US 7,582,736 B2
(45) Date of Patent: Sep. 1, 2009

(54) PROSTATE CANCER SPECIFIC INTERNALIZING HUMAN ANTIBODIES

(75) Inventors: Bin Liu, Hercules, CA (US); James D. Marks, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/972,130

(22) Filed: Jan. 10, 2008

(65) Prior Publication Data

US 2009/0010841 A1   Jan. 8, 2009

Related U.S. Application Data

(62) Division of application No. 11/021,438, filed on Dec. 21, 2004, now Pat. No. 7,335,744.

(60) Provisional application No. 60/532,433, filed on Dec. 23, 2003.

(51) Int. Cl.
  *C12P 21/08* (2006.01)

(52) U.S. Cl. .............. 530/387.3; 530/387.7; 530/388.2; 530/391.3; 530/391.7; 424/133.1; 424/136.1; 424/155.1

(58) Field of Classification Search .............. 530/387.3, 530/387.7, 388.2, 388.8, 391.3, 391.7; 424/133.1, 424/136.1, 155.1
See application file for complete search history.

(56) References Cited

U.S. PATENT DOCUMENTS

| | | |
|---|---|---|
| 4,863,851 A | 9/1989 | McEman et al. |
| 5,227,471 A | 7/1993 | Wright, Jr. |
| 5,314,996 A | 5/1994 | Wright, Jr. |
| 5,763,202 A | 6/1998 | Horoszewicz |
| 6,307,026 B1 | 10/2001 | King et al. |
| 6,790,938 B1 | 9/2004 | Berchtold et al. |
| 6,881,822 B2 | 4/2005 | Reiter et al. |
| 6,887,660 B2 | 5/2005 | Xu et al. |
| 6,890,749 B2 | 5/2005 | Billing-Medel et al. |
| 6,893,818 B1 | 5/2005 | Afar et al. |
| 6,900,022 B1 | 5/2005 | French et al. |
| 6,933,114 B2 | 8/2005 | Lupold et al. |
| 6,943,235 B1 | 9/2005 | Afar et al. |
| 6,946,133 B1 | 9/2005 | Schlom et al. |
| 6,953,668 B1 | 10/2005 | Israeli et al. |

OTHER PUBLICATIONS

Wang et al (Prot. Exp. Purf., 23:419-425, 2001).*
Heath et al., PNAS, 94:469-474, 1997.
Greenspan et al. (Nature Biotechnology. 1999; 7: 936-937).
Daniel et al (Virology, 202:540-549, 1994).
Liu et al (Cancer Research, 64:704-710, Jan. 15, 2004).
George et al. (Circulation. 1998; 97: 900-906).
Mariuzza et al. (Annu. Rev. Biophys. Chem. 1987; 16: 139-159).
Gussow et al. (Methods in Enzymology. 1991; 203; 203: 99-121).
Giusti et al. (Proc. Natl. Acad. Sci. USA. May 1987; 84 (9): 2926-2930).
Chien et al. (Proc. Natl. Acad. Sci. USA. Jul. 1989; 86 (14): 5532-5536.
Caldas et al. (Mol. Immunol. May 2003; 39 (15): 941-952).
Liu et al (Cancer Research, 58:4055-4060, 1998).
Gao et al (Journal of Immunological Methods, 274:185-197, Mar. 2003).
Daghighian et al (Journal of Nuclear Medicine, 37(6):1052-1057, 1996).
Becerril et al. (1999) "Toward Selection of Internalizing Antibodies from Phage Libraries." Biochemical and Biophysicay Research Communications, 255: 386-393.
Cai and Garen (1995) "Anti-melanoma antibodies from melanoma patients immunized with genetically modified antologous tumor cells: Selection of specific antibodies from single-chain Fv fusion phage libraries." Proceedings of the National Academy of Sciences USA, 92: 6537-6541.
Cai and Garen (1996) "A melanoma-specific VH antibody cloned from a fusion phage library of a vaccinated melanoma patient." Proceeding of the National Academy of Sciences USA 93: 6280-6285.
Carter (2001) "Improving the Efficacy of Antibody-Based Cancer Therapies." Nature Reviews Cancer, 1: 118-129.
Coleman (2002) "Future Directions in the reatment and Prevention of Bone Metastases." American Journal of Clinical Oncology, 25(6 Suppl 1): S32-S38.
Dhanasekaran et al. (2001) "Delineation of prognostic biomakers in prostate cancer." Nature, 412: 822-826.
Fair et al. (1997) "Prostate-Specific Membrane Antigen." Prostate, 32: 140-148.
Gao et al. (2003) "De novo identification of tumor-specific internalizing human antibody—receptor pairs by phage-display methods." Journal of Immunological Methods, 274: 185-197.
Heitner et al. (2001) "Selection of cell binding and internalizing epidermal growth factor receptor antibodies from a phage-display library." Journal of Immunological Methods, 248: 17-30.
Hoogenboom (2002) "Overview of Antibody Phage-Display Technology and Its Applications." Methods in Molecular Biology, Chapter 1, vol. 178: 1-37.
Hubert et al. (1999) "STEAP: A prostate-specific cell-surface antigen highly expressed in human prostate tumors." Proceeding of the National Academy of Sciences USA, 96(25): 14523-14528.

(Continued)

*Primary Examiner*—Stephen L Rawlings
*Assistant Examiner*—Brad Duffy
(74) *Attorney, Agent, or Firm*—Weaver Austin Villeneuve & Sampson LLP; Tom Hunter

(57) ABSTRACT

This invention provides novel prostate cancer specific internalizing human antibodies. The antibodies are useful by themselves to prevent growth and/or proliferation of prostate cancer cells. The antibodies can also be formulated as chimeric molecules to direct an effector (e.g. a cytotoxin, an imaging reagent, a drug, etc.) to a prostate tumor site.

20 Claims, 11 Drawing Sheets

OTHER PUBLICATIONS

Huie et al. (2001) "Antibodies to human fetal erythroid cells from a nonimmune phage antibody library." Proceeding of the National Academy of Sciences USA, 98(5): 2682-2687.

Jemal et al. (2003) "Cancer Statistics, 2003." CA A Cancer Journal for Clinicians, 53: 5-26.

Lee et al. (2002) "Phage-Display Selection of a Human Single-Chain Fv Antibody Highly Specific for Melanoma and Breast Cancer Cells Using a Chemoenzymatically Synthesized GM3—Carbohydrate Antigen." Journal of the American Chemistry Society, 124: 12439-12446.

Li et al. (2001) "Isolation of the Melanoma-Associated Antigen p23 Using Antibody Phage Display." Journal of Immunology, 166: 432-438.

Liu and Marks (2000) "Applying Phage Antibodies to Proteomics: Selecting Single Chain Fv Antibodies to Antigens Blotted on Nitocellulose." Analytical Biochemistry, 286: 119-128.

Liu et al. (2002) "Toward Proteome-wide Production of Monoclonal Antibody by Phage Display." Journal of Molecular Biology, 315: 1063-1073.

Nielsen et al. (2002) "Therapeutic efficacy of anti-ErbB2 immunoliposomes targeted by a phage antibody selected for cellular endocytosis." Biochimica et Biophysica Acta, 1591: 109-118.

O'Connell et al. (2002) "Phage versus Phagemid Libraries for Generation of Human Monoclonal Antibodies." Journal of Molecular Biology, 321: 49-56.

Poul et al. (2000) "Selection of Tumor-Spceific Internalizing Human Antibodies from Phage Libraries." Journal of Molecular Biology, 301: 1149-1161.

Reiter et al. (1998) "Prostate stem cell antigen: A cell surface marker overexpressed in prostate cancer." Proceeding of the National Academy of Sciences USA, 95: 1735-1740.

Saffran et al. (2001) "Anti-PSCA mAbs inhibit tumor growth and metastasis formation and prolong the curvival of mice bearing human prostate cancer xenografts." Proceeding of the National Academy of Sciences USA, 98(5): 2658-2663.

Theocharis (2002) "Human colon adenocarcinoma is associated with specific post-translational modifications of versican and decorin." ica et Biophysica Acta, 1588: 165-172.

Xu et al. (2000) "PSGR, a Novel Prostate-specific Gene with Homology to a G Protein-coupled Receptor, Is Overexpressed in Prostate Cancer." Cancer Research, 60: 6568-6572.

* cited by examiner

| Antibody | Sequence | SEQ ID NO |
|---|---|---|
| A33 | QVQLQQSGGGLVQPGRSLRLSCAASGFAFDDYAMHWVRQAPGKGLEWVSGISWNSGSIGYADSVKGRFTISRDNAKNSLYLQMNSLRAEDTALYYCAKAQGSSWYYYGMDVWGQGTMVTVSSGGGGSGGGGSGGGGSDVVMTQDPAVSVALGQTVRITCQGDSLRSYYASWYQQKPGQAPVLVIYGKNNRPSGIPDRFSGSSSGNTASLTITGAQAEDEADYYCNSRDSSGNPWVFGGGTKLTVL | 22 |
| M10A12 | QVQLVESGGGVVQPGRSLRLSCTASGFTFSSYGMHWVRQAPGKGLEWVAVISYDGSNKYYADSVKGRFTISRDNSKNTLYLQMNSLRAEDTAVYYCARGGRYSSNWFSYYYYGMDVWGQGTTVTVSSGGGGSGGGGSGGGGSSSELTQDPAVSVALGQTVRITCQGDSLRSYYASWYQQKPGQAPLLVIYGENNRPSGIPDRFSGSSSGNTAFLTISRVEAGDEADYYCQVWDSSSDHPGVVFGGGTKVTVL | 23 |
| M9E4 | QVQLQQSGGGLVQPGRSLRLSCAASGFTFDDYAMHWVRQAPGKGLEWVSGISWNSGSIGYADSVKGRFTISRDNAKNSLYLQMNSLRVEDTAVYYCARDNWGSIDYWGQGTLVTVSSGGGGSGGGGSGGGGSSSELTQDPAVSVALGQTVRITCQGDSLRNYFVSWFQKKPGQAPVLVVYDDTDRPSGIPERFSGSNSGNTATLTISRIEAGDEADYYCQLWDTGSDHAVVFGGGTKLTVL | 24 |
| OA12 | QVQLQESGGGVVQPGRSLRLSCAASGFTFSSYDMHWVRQAPGKGLEWVAVIWYDGSNKYYADSVKGRFTISRDNSKNTLYLQMNSLRAEDTAVYYCARDRYGDYLFDYWGQGTLVTVSSGGGGSGGGGSGGGGSQSVLTQPPSVSGAPGQRVTISCTGRSSNIGAGYDIHWYQHLPGTAPKLLIYGNSNRPSGVPDRFSGSKSGTSASLAISGLQSEDEADYYCAAWDDSLNAVVFGGGTKVTVL | 25 |

*Fig. 1A*

| Antibody | Sequence | SEQ ID NO |
|---|---|---|
| M11G12 | QVQLQESGGGLVQPGGSLRLSCAASGFTFSSYAMS WVRQAPGKGLEWVSAISGSGGSTYYADSVKGRFTI SRDNSKNTLYLQMSSLRAEDTAFYYCANSAYTGG WYDYWGHGTLVTVSSGGGGSGGGGSGGGGSSSEL TQDPAVSVALGQTVKITCQGDSLRTYYASWYQQRP GQAPVLVIYGENSRPSGIPDRFSGSSSGNTASLTITG AQAEDEADYYCNSRDSSGNHLRVFGGGTKLTVL | 26 |
| M11F12 | QVQLVQSGGGLVQPGGSLRLSCAASGFTVSSNYMS WVRQAPGKGLEWVSVISGTGGSTYYADSVKGRFTI SRDNSKNTVYLQMNSLRAEDTAVYYCARENWFLD YWGQGALVTVSSGGGGSGGGGSGGGGSQSALTQ DPAVSVALGQTVRITCRGDSLGTYYATWYQQKPG QAPVLVIYGENNRPSGIPDRFSGSSSGNTASLTITGA QAEDEADYYCNSRDSSGNHVVFGRGTKLTVL | 27 |
| C10 | QVQLVESGGGLVKPGGSLRLSCAASGFTFSSYAMH WVRQAPGKGLEWVAVISYDGSNKYYADSVKGRFT ISRDNSKNTLYLQMNSLRAEDTAVYFCVRPSDSGW SFEHWGQGTLVPVSSGGGGSGGGGSGGGGSSSEL TQDPAVSVALGQTVRITCQGDSLRSYYASWYQQKP GQAPVLVIYGKNNRPSGIPDRFSGSSSGNTASLTITG AQAEDEADYYCNSRDSSGNRNWVFGGGTKLAVL | 28 |

*Fig. 1B*

```
                        SEQUENCE LISTING

<160> NUMBER OF SEQ ID NOS: 30

<210> SEQ ID NO 1
<211> LENGTH: 8
<212> TYPE: PRT
<213> ORGANISM: Artificial
<220> FEATURE:
<223> OTHER INFORMATION: Synthetic epitope tag.

<400> SEQUENCE: 1

Asp Tyr Lys Asp Asp Asp Asp Lys
1               5

<210> SEQ ID NO 2
<211> LENGTH: 122
<212> TYPE: PRT
<213> ORGANISM: Artificial
<220> FEATURE:
<223> OTHER INFORMATION: Domain of synthetic human antibody.

<400> SEQUENCE: 2

Gln Val Gln Leu Gln Gln Ser Gly Gly Gly Leu Val Gln Pro Gly Arg
1               5                   10                  15

Ser Leu Arg Leu Ser Cys Ala Ala Ser Gly Phe Ala Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

Ala Lys Ala Gln Gly Ser Ser Trp Tyr Tyr Tyr Gly Met Asp Val Trp
            100                 105                 110

Gly Gln Gly Thr Met Val Thr Val Ser Ser
        115                 120

<210> SEQ ID NO 3
<211> LENGTH: 127
<212> TYPE: PRT
<213> ORGANISM: Artificial
<220> FEATURE:
<223> OTHER INFORMATION: Domain of synthetic human antibody.

<400> SEQUENCE: 3

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
            100                 105                 110

Gly Met Asp Val Trp Gly Gln Gly Thr Thr Val Thr Val Ser Ser
        115                 120                 125

<210> SEQ ID NO 4
<211> LENGTH: 117
<212> TYPE: PRT
<213> ORGANISM: Artificial
<220> FEATURE:
<223> OTHER INFORMATION: Domain of synthetic human antibody.

<400> SEQUENCE: 4

Gln Val Gln Leu Gln Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Asn Trp Gly Ser Ile Asp Tyr Trp Gly Gln Gly Thr Leu
            100                 105                 110

Val Thr Val Ser Ser
        115

<210> SEQ ID NO 5
<211> LENGTH: 119
<212> TYPE: PRT

```
<213> ORGANISM: Artificial
<220> FEATURE:
<223> OTHER INFORMATION: Domain of synthetic human antibody.

<400> SEQUENCE: 5

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Gly Asp Tyr Leu Phe Asp Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial
<220> FEATURE:
<223> OTHER INFORMATION: Domain of synthetic human antibody.

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser
        115

<210> SEQ ID NO 7
<211> LENGTH: 116
<212> TYPE: PRT
<213> ORGANISM: Artificial
<220> FEATURE:
<223> OTHER INFORMATION: Domain of synthetic human antibody.

<400> SEQUENCE: 7

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30
```

Tyr Met Ser Trp Val Arg Gln Ala Pro Gly Lys Gly Leu Glu Trp Val
            35                  40                  45

Ser Val Ile Ser Gly Thr Gly Gly Ser Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Glu Asn Trp Phe Leu Asp Tyr Trp Gly Gln Gly Ala Leu Val
            100                 105                 110

Thr Val Ser Ser
        115

<210> SEQ ID NO 8
<211> LENGTH: 119
<212> TYPE: PRT
<213> ORGANISM: Artificial
<220> FEATURE:
<223> OTHER INFORMATION: Domain of synthetic human antibody.

<400> SEQUENCE: 8

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Val Arg Pro Ser Asp Ser Gly Trp Ser Phe Glu His Trp Gly Gln Gly
            100                 105                 110

Thr Leu Val Pro Val Ser Ser
        115

<210> SEQ ID NO 9
<211> LENGTH: 108
<212> TYPE: PRT
<213> ORGANISM: Artificial
<220> FEATURE:
<223> OTHER INFORMATION: Domain of synthetic human antibody.

<400> SEQUENCE: 9

Asp Val Val Met Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro

```
                    85                  90                  95
Trp Val Phe Gly Gly Gly Thr Lys Leu Thr Val Leu
                100                 105

<210> SEQ ID NO 10
<211> LENGTH: 110
<212> TYPE: PRT
<213> ORGANISM: Artificial
<220> FEATURE:
<223> OTHER INFORMATION: Domain of synthetic human antibody.

<400> SEQUENCE: 10

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
        35                  40                  45

Gly Glu Asn Asn Arg Pro Ser Gly Ile Pro Asp Arg Phe Ser Gly Ser
    50                  55                  60

Ser Ser Gly Asn Thr Ala Phe Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Gly Val Val Phe Gly Gly Gly Thr Lys Val Thr Val Leu
            100                 105                 110

<210> SEQ ID NO 11
<211> LENGTH: 109
<212> TYPE: PRT
<213> ORGANISM: Artificial
<220> FEATURE:
<223> OTHER INFORMATION: Domain of synthetic human antibody.

<400> SEQUENCE: 11

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Phe Val
            20                  25                  30

Ser Trp Phe Gln Lys Lys Pro Gly Gln Ala Pro Val Leu Val Val Tyr
        35                  40                  45

Asp Asp Thr Asp Arg Pro Ser Gly Ile Pro Glu Arg Phe Ser Gly Ser
    50                  55                  60

Asn Ser Gly Asn Thr Ala Thr Leu Thr Ile Ser Arg Ile Glu Ala Gly
65                  70                  75                  80

Asp Glu Ala Asp Tyr Tyr Cys Gln Leu Trp Asp Thr Gly Ser Asp His
                85                  90                  95

Ala Val Val Phe Gly Gly Gly Thr Lys Leu Thr Val Leu
            100                 105

<210> SEQ ID NO 12
<211> LENGTH: 111
<212> TYPE: PRT
<213> ORGANISM: Artificial
<220> FEATURE:
<223> OTHER INFORMATION: Domain of synthetic human antibody.

<400> SEQUENCE: 12

Gln Ser Val Leu Thr Gln Pro Pro Ser Val Ser Gly Ala Pro Gly Gln
1               5                   10                  15
```

```
Arg Val Thr Ile Ser Cys Thr Gly Arg Ser Ser Asn Ile Gly Ala Gly
            20                  25                  30

Tyr Asp Ile His Trp Tyr Gln His Leu Pro Gly Thr Ala Pro Lys Leu
            35                  40                  45

Leu Ile Tyr Gly Asn Ser Asn Arg Pro Ser Gly Val Pro Asp Arg Phe
            50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Ser
            85                  90                  95

Leu Asn Ala Val Val Phe Gly Gly Thr Lys Val Thr Val Leu
            100                 105                 110

<210> SEQ ID NO 13
<211> LENGTH: 109
<212> TYPE: PRT
<213> ORGANISM: Artificial
<220> FEATURE:
<223> OTHER INFORMATION: Domain of synthetic human antibody.

<400> SEQUENCE: 13

Ser Ser Glu Leu Thr Gln Asp Pro Ala Val Ser Val Ala Leu Gly Gln
1               5                   10                  15

Thr Val Lys Ile Thr Cys Gln Gly Asp Ser Leu Arg Thr Tyr Tyr Ala
            20                  25                  30

Ser Trp Tyr Gln Gln Arg Pro Gly Gln Ala Pro Val Leu Val Ile Tyr
            35                  40                  45

Gly Glu Asn Ser Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
            85                  90                  95

Leu Arg Val Phe Gly Gly Gly Thr Lys Leu Thr Val Leu
            100                 105

<210> SEQ ID NO 14
<211> LENGTH: 108
<212> TYPE: PRT
<213> ORGANISM: Artificial
<220> FEATURE:
<223> OTHER INFORMATION: Domain of synthetic human antibody.

<400> SEQUENCE: 14

Gln Ser Ala Leu Thr Gln Asp Pro Ala Val Ser Val Ala Leu Gly Gln
1               5                   10                  15

Thr Val Arg Ile Thr Cys Arg Gly Asp Ser Leu Gly Thr Tyr Tyr Ala
            20                  25                  30

Thr Trp Tyr Gln Gln Lys Pro Gly Gln Ala Pro Val Leu Val Ile Tyr
            35                  40                  45

Gly Glu Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
            85                  90                  95

Val Val Phe Gly Arg Gly Thr Lys Leu Thr Val Leu
```

```
<210> SEQ ID NO 15
<211> LENGTH: 109
<212> TYPE: PRT
<213> ORGANISM: Artificial
<220> FEATURE:
<223> OTHER INFORMATION: Domain of synthetic human antibody.

<400> SEQUENCE: 15

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Arg
                85                  90                  95

Asn Trp Val Phe Gly Gly Gly Thr Lys Leu Ala Val Leu
            100                 105

<210> SEQ ID NO 16
<211> LENGTH: 12
<212> TYPE: PRT
<213> ORGANISM: Artificial
<220> FEATURE:
<223> OTHER INFORMATION: Peptide Linker.

<400> SEQUENCE: 16

Gly Gly Gly Ser Gly Gly Gly Ser Gly Gly Gly Ser
1               5                   10

<210> SEQ ID NO 17
<211> LENGTH: 5
<212> TYPE: PRT
<213> ORGANISM: Artificial
<220> FEATURE:
<223> OTHER INFORMATION: Peptide linker.

<400> SEQUENCE: 17

Gly Gly Gly Gly Ser
1               5

<210> SEQ ID NO 18
<211> LENGTH: 5
<212> TYPE: PRT
<213> ORGANISM: Artificial
<220> FEATURE:
<223> OTHER INFORMATION: Peptide translocation signal sequence.

<400> SEQUENCE: 18

Arg Glu Asp Leu Lys
1               5

<210> SEQ ID NO 19
<211> LENGTH: 4
<212> TYPE: PRT
<213> ORGANISM: Artificial
<220> FEATURE:
<223> OTHER INFORMATION: Peptide translocation signal sequence.
```

-continued

```
<400> SEQUENCE: 19

Arg Glu Asp Leu
1

<210> SEQ ID NO 20
<211> LENGTH: 4
<212> TYPE: PRT
<213> ORGANISM: Artificial
<220> FEATURE:
<223> OTHER INFORMATION: Peptide translocation signal sequence.

<400> SEQUENCE: 20

Arg Asp Glu Leu
1

<210> SEQ ID NO 21
<211> LENGTH: 4
<212> TYPE: PRT
<213> ORGANISM: Artificial
<220> FEATURE:
<223> OTHER INFORMATION: Peptide translocation signal sequence.

<400> SEQUENCE: 21

Lys Asp Glu Leu
1

<210> SEQ ID NO 22
<211> LENGTH: 245
<212> TYPE: PRT
<213> ORGANISM: Artificial
<220> FEATURE:
<223> OTHER INFORMATION: Recombinant single-chain human antibody.

<400> SEQUENCE: 22

Gln Val Gln Leu Gln Gln Ser Gly Gly Gly Leu Val Gln Pro Gly Arg
1               5                   10                  15

Ser Leu Arg Leu Ser Cys Ala Ala Ser Gly Phe Ala Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ala Gln Gly Ser Ser Trp Tyr Tyr Tyr Gly Met Asp Val Trp
            100                 105                 110

Gly Gln Gly Thr Met Val Thr Val Ser Gly Gly Gly Ser Gly
        115                 120                 125

Gly Gly Gly Ser Gly Gly Gly Ser Asp Val Val Met Thr Gln Asp
    130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
            180                 185                 190

Gly Ile Pro Asp Arg Phe Ser Gly Ser Ser Ser Gly Asn Thr Ala Ser
```

Leu Thr Ile Thr Gly Ala Gln Ala Glu Asp Glu Ala Asp Tyr Tyr Cys
210                 215                 220

Asn Ser Arg Asp Ser Ser Gly Asn Pro Trp Val Phe Gly Gly Thr
225                 230                 235                 240

Lys Leu Thr Val Leu
245

<210> SEQ ID NO 23
<211> LENGTH: 252
<212> TYPE: PRT
<213> ORGANISM: Artificial
<220> FEATURE:
<223> OTHER INFORMATION: Recombinant single-chain human antibody.

<400> SEQUENCE: 23

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Gly Ser Gly Gly Gly Gly Ser Ser Ser
    130                 135                 140

Glu Leu Thr Gln Asp Pro Ala Val Ser Val Ala Leu Gly Gln Thr Val
145                 150                 155                 160

Arg Ile Thr Cys Gln Gly Asp Ser Leu Arg Ser Tyr Tyr Ala Ser Trp
                165                 170                 175

Tyr Gln Gln Lys Pro Gly Gln Ala Pro Leu Leu Val Ile Tyr Gly Glu
            180                 185                 190

Asn Asn Arg Pro Ser Gly Ile Pro Asp Arg Phe Ser Gly Ser Ser Ser
        195                 200                 205

Gly Asn Thr Ala Phe Leu Thr Ile Ser Arg Val Glu Ala Gly Asp Glu
    210                 215                 220

Ala Asp Tyr Tyr Cys Gln Val Trp Asp Ser Ser Ser Asp His Pro Gly
225                 230                 235                 240

Val Val Phe Gly Gly Gly Thr Lys Val Thr Val Leu
                245                 250

<210> SEQ ID NO 24
<211> LENGTH: 241
<212> TYPE: PRT
<213> ORGANISM: Artificial
<220> FEATURE:
<223> OTHER INFORMATION: Recombinant single-chain human antibody.

<400> SEQUENCE: 24

```
Gln Val Gln Leu Gln Gln Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Asp Asn Trp Gly Ser Ile Asp Tyr Trp Gly Gln Gly Thr Leu
             100                 105                 110

Val Thr Val Ser Ser Gly Gly Gly Ser Gly Gly Gly Gly Ser Gly
             115                 120                 125

Gly Gly Gly Ser Ser Glu Leu Thr Gln Asp Pro Ala Val Ser Val
         130                 135                 140

Ala Leu Gly Gln Thr Val Arg Ile Thr Cys Gln Gly Asp Ser Leu Arg
145                 150                 155                 160

Asn Tyr Phe Val Ser Trp Phe Gln Lys Lys Pro Gly Gln Ala Pro Val
                 165                 170                 175

Leu Val Val Tyr Asp Asp Thr Asp Arg Pro Ser Gly Ile Pro Glu Arg
                 180                 185                 190

Phe Ser Gly Ser Asn Ser Gly Asn Thr Ala Thr Leu Thr Ile Ser Arg
             195                 200                 205

Ile Glu Ala Gly Asp Glu Ala Asp Tyr Tyr Cys Gln Leu Trp Asp Thr
         210                 215                 220

Gly Ser Asp His Ala Val Val Phe Gly Gly Thr Lys Leu Thr Val
225                 230                 235                 240

Leu

<210> SEQ ID NO 25
<211> LENGTH: 245
<212> TYPE: PRT
<213> ORGANISM: Artificial
<220> FEATURE:
<223> OTHER INFORMATION: Recombinant single-chain human antibody.

<400> SEQUENCE: 25

Gln Val Gln Leu Gln Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Tyr Gly Asp Tyr Leu Phe Asp Tyr Trp Gly Gln Gly
             100                 105                 110

Thr Leu Val Thr Val Ser Ser Gly Gly Gly Gly Ser Gly Gly Gly Gly
```

```
              115                 120                 125
Ser Gly Gly Gly Ser Gln Ser Val Leu Thr Gln Pro Ser Val
        130                 135                 140
Ser Gly Ala Pro Gly Gln Arg Val Thr Ile Ser Cys Thr Gly Arg Ser
145                 150                 155                 160
Ser Asn Ile Gly Ala Gly Tyr Asp Ile His Trp Tyr Gln His Leu Pro
                165                 170                 175
Gly Thr Ala Pro Lys Leu Leu Ile Tyr Gly Asn Ser Asn Arg Pro Ser
                180                 185                 190
Gly Val Pro Asp Arg Phe Ser Gly Ser Lys Ser Gly Thr Ser Ala Ser
                195                 200                 205
Leu Ala Ile Ser Gly Leu Gln Ser Glu Asp Glu Ala Asp Tyr Tyr Cys
        210                 215                 220
Ala Ala Trp Asp Asp Ser Leu Asn Ala Val Val Phe Gly Gly Gly Thr
225                 230                 235                 240

Lys Val Thr Val Leu
                245

<210> SEQ ID NO 26
<211> LENGTH: 243
<212> TYPE: PRT
<213> ORGANISM: Artificial
<220> FEATURE:
<223> OTHER INFORMATION: Recombinant single-chain human antibody.

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
                100                 105                 110

Thr Leu Val Thr Val Ser Ser Gly Gly Gly Ser Gly Gly Gly Gly
            115                 120                 125

Ser Gly Gly Gly Gly Ser Ser Glu Leu Thr Gln Asp Pro Ala Val
        130                 135                 140

Ser Val Ala Leu Gly Gln Thr Val Lys Ile Thr Cys Gln Gly Asp Ser
145                 150                 155                 160

Leu Arg Thr Tyr Tyr Ala Ser Trp Tyr Gln Gln Arg Pro Gly Gln Ala
                165                 170                 175

Pro Val Leu Val Ile Tyr Gly Glu Asn Ser Arg Pro Ser Gly Ile Pro
                180                 185                 190

Asp Arg Phe Ser Gly Ser Ser Ser Gly Asn Thr Ala Ser Leu Thr Ile
                195                 200                 205

Thr Gly Ala Gln Ala Glu Asp Glu Ala Asp Tyr Tyr Cys Asn Ser Arg
        210                 215                 220

Asp Ser Ser Gly Asn His Leu Arg Val Phe Gly Gly Gly Thr Lys Leu
```

```
                225                 230                 235                 240

Thr Val Leu

<210> SEQ ID NO 27
<211> LENGTH: 245
<212> TYPE: PRT
<213> ORGANISM: Artificial
<220> FEATURE:
<223> OTHER INFORMATION: Recombinant single-chain human antibody.

<400> SEQUENCE: 27

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Gly Asp Tyr Leu Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Gly Ala Pro Gly Gln Arg Val Thr Ile Ser Cys Thr Gly Arg Ser
145                 150                 155                 160

Ser Asn Ile Gly Ala Gly Tyr Asp Ile His Trp Tyr Gln His Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala Asp Tyr Tyr Cys
    210                 215                 220

Ala Ala Trp Asp Asp Ser Leu Asn Ala Val Val Phe Gly Gly Gly Thr
225                 230                 235                 240

Lys Val Thr Val Leu
                245

<210> SEQ ID NO 28
<211> LENGTH: 243
<212> TYPE: PRT
<213> ORGANISM: Artificial
<220> FEATURE:
<223> OTHER INFORMATION: Recombinant single-chain human antibody.

<400> SEQUENCE: 28

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Phe Tyr Tyr Cys
                 85                  90                  95

Ala Asn Ser Ala Tyr Thr Gly Gly Trp Tyr Asp Tyr Trp Gly His Gly
            100                 105                 110

Thr Leu Val Thr Val Ser Ser Gly Gly Gly Ser Gly Gly Gly Gly
            115                 120                 125

Ser Gly Gly Gly Ser Ser Glu Leu Thr Gln Asp Pro Ala Val
            130                 135                 140

Ser Val Ala Leu Gly Gln Thr Val Lys Ile Thr Cys Gln Gly Asp Ser
145                 150                 155                 160

Leu Arg Thr Tyr Tyr Ala Ser Trp Tyr Gln Gln Arg Pro Gly Gln Ala
                165                 170                 175

Pro Val Leu Val Ile Tyr Gly Glu Asn Ser Arg Pro Ser Gly Ile Pro
            180                 185                 190

Asp Arg Phe Ser Gly Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
210                 215                 220

Asp Ser Ser Gly Asn His Leu Arg Val Phe Gly Gly Gly Thr Lys Leu
225                 230                 235                 240

Thr Val Leu

<210> SEQ ID NO 29
<211> LENGTH: 239
<212> TYPE: PRT
<213> ORGANISM: Artificial
<220> FEATURE:
<223> OTHER INFORMATION: Recombinant single-chain human antibody.

<400> SEQUENCE: 29

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Ser Gly Thr Gly Gly Ser Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Arg Glu Asn Trp Phe Leu Asp Tyr Trp Gly Gln Gly Ala Leu Val
            100                 105                 110

Thr Val Ser Ser Gly Gly Gly Gly Ser Gly Gly Gly Gly Ser Gly Gly
            115                 120                 125

Gly Gly Ser Gln Ser Ala Leu Thr Gln Asp Pro Ala Val Ser Val Ala
            130                 135                 140

Leu Gly Gln Thr Val Arg Ile Thr Cys Arg Gly Asp Ser Leu Gly Thr
145                 150                 155                 160
```

```
Tyr Tyr Ala Thr Trp Tyr Gln Gln Lys Pro Gly Gln Ala Pro Val Leu
                165                 170                 175

Val Ile Tyr Gly Glu Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Arg Asp Ser Ser
    210                 215                 220

Gly Asn His Val Val Phe Gly Arg Gly Thr Lys Leu Thr Val Leu
225                 230                 235

<210> SEQ ID NO 30
<211> LENGTH: 243
<212> TYPE: PRT
<213> ORGANISM: Artificial
<220> FEATURE:
<223> OTHER INFORMATION: Recombinant single-chain human antibody.

<400> SEQUENCE: 30

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
            85                  90                  95

Val Arg Pro Ser Asp Ser Gly Trp Ser Phe Glu His Trp Gly Gln Gly
        100                 105                 110

Thr Leu Val Pro Val Ser Ser Gly Gly Gly Ser Gly Gly Gly Gly
        115                 120                 125

Ser Gly Gly Gly Gly Ser Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
            165                 170                 175

Pro Val Leu Val Ile Tyr Gly Lys Asn Asn Arg Pro Ser Gly Ile Pro
        180                 185                 190

Asp Arg Phe Ser Gly Ser Ser Ser Gly Asn Thr Ala Ser Leu Thr Ile
    195                 200                 205

Thr Gly Ala Gln Ala Glu Asp Glu Ala Asp Tyr Tyr Cys Asn Ser Arg
    210                 215                 220

Asp Ser Ser Gly Asn Arg Asn Trp Val Phe Gly Gly Gly Thr Lys Leu
225                 230                 235                 240

Ala Val Leu
```

PROSTATE CANCER SPECIFIC INTERNALIZING HUMAN ANTIBODIES

CROSS-REFERENCE TO RELATED APPLICATIONS

This application is a Divisional of U.S. Ser. No. 11/021,438, filed on Dec. 21, 2004, which claims priority to and benefit of U.S. Ser. No. 60/532,433, filed on Dec. 23, 2003, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support by Grant No. CA89520, awarded by the National Institutes of Health. The Government of the United States of America has certain rights in this invention.

FIELD OF THE INVENTION

This invention pertains to the field of antibodies, immunodiagnostics, and immunotherapeutics. In particular, this invention pertains to the discovery of prostate cancer specific internalizing antibodies.

BACKGROUND OF THE INVENTION

Cancer cells differ from normal cells in a variety of ways, one of which is the molecular composition of the cell surface. These differences may be exploited in the development of targeted therapeutics. In principle, a variety of anti-neoplastic agents can be attached to affinity molecules, such as monoclonal antibodies (mAbs), which recognize tumor-specific cell surface molecules to achieve targeted killing (Carter (2001) *Nature Rev Cancer*, 1: 118-129). The epitope space at the tumor cell surface, however, is highly complex, including, in addition to proteins, carbohydrate determinants and other post-translational modification products which are difficult to probe by gene expression-based approaches (Theocharis (2002) *Biochim Biophys Acta.*, 1588: 165-172; Lee et al. (2002) *J Am Chem Soc*, 124: 12439-12446). For carcinoma of the prostate (CaP), there are few known specific cell surface markers, and even fewer specific markers for hormone refractory CaP (Fair et al. (1997) *Prostate*. 32: 140-148; Dhanasekaran et al. (2001) *Nature*, 412: 822-826; Xu et al. (2000) *Cancer Res.*, 60: 6568-6572; Hubert et al. (1999) *Proc Natl Acad Sci USA.*, 96: 14523-14528; Saffran et al. (2001) *Proc Natl Acad Sci USA.*, 98: 2658-2663; Reiter et al. (1998) *Proc Natl Acad Sci USA.*, 95: 1735-1740). Moreover, despite recent advances in early diagnosis and treatment, prostate cancer remains the most common and second most lethal tumor in American men (Jemal et al. (2003) *CA Cancer J Clin*, 53: 5-26), and no curative treatment currently exists for metastatic disease (Coleman (2002) *Am J Clin Oncol*, 25: S32-38, 2002).

Tumor specific epitope space may be efficiently mapped by complementary mAbs. Phage display of non-immune single chain Fv (scFv) or Fab antibody repertoires has proven to be an important tool for generating highly specific antibody combining sites that may be readily converted into mAbs (Marks et al. (1991) *J Mol Biol*, 222: 581-597; de Haard et al. (1990) *Nature*, 348: 552-554; Barbas et al. (1991) *Proc Natl Acad Sci USA*, 88: 7978-7982), if needed. Non-immune phage libraries are derived from naïve human lymphocytes, thus recapitulate the primary immune response (Marks et al. (1991) *J Mol Biol*, 222: 581-597), and overcome difficulties with generating antibodies to evolutionarily conserved, or 'self', antigens which may comprise a large portion of tumor antigens (Sheets et al. (1998) *Proc Natl Acad Sci USA*, 95: 6157-6162; Griffiths et al. (1993) *Embo J*, 12: 725-734). This broader repertoire of specificities allows a less biased and more thorough mapping of epitope space (Amersdorfer et al. (1993) *Vaccine*, 20: 1640-1648). MAbs to tumor antigens have been isolated by directly selecting phage libraries on native and modified tumor antigens (Hoogenboom (2002) *Methods Mol Biol*, 178: 1-37). The success of direct cell selections in generating tumor targeting mAbs has been limited, however, by high non-specific binding of phage to cell surfaces and by high representation of phage antibody binding to common cell surface molecules (Hoogenboom (2002) *Methods Mol Biol*, 178: 1-37; Gao et al. (2003) *J Immunol Methods*, 274: 185-197).

Recently we reported that phage antibody selections on cells could be significantly improved by selecting for mAbs that trigger receptor mediated endocytosis, since endocytosed phage may be recovered from within the tumor cell after stripping non-specific binders from the cell surface (Becerril et al. (1999) *Biochem Biophys Res Commun*, 255: 386-393). Besides increasing selection efficiency, this approach generates mAbs that have desirable biologic properties: receptor mediated intracellular drug delivery, induction of apoptosis, or inhibition of proliferation (Nielsen et al. (2002) *Biochim Biophys Acta.*, 1591: 109-118; Poul et al. (2000) *J Mol Biol*, 301: 1149-1161; Heitner et al. (2001) *J Immunol Methods*, 248: 17-30). We applied this approach to breast tumor cells and generated mAbs to a number of known internalizing receptors, including EGFR and ErbB2 (Poul et al. (2000) *J Mol Biol*, 301: 1149-1161; Heitner et al. (2001) *J Immunol Methods*, 248: 17-30). To broaden applicability, libraries of phage displaying multiple copies of scFv were engineered (O'Connell et al. (2002) *J Mol Biol*, 321: 49-56; Liu and Marks (2000) *Anal Biochem*, 286: 119-128; Huie et al. (2001) *Proc Natl Acad Sci USA.*, 98: 2682-2687), which unlike existing phage libraries can crosslink receptors, allowing more efficient phage endocytosis (Becerril et al. (1999) *Biochem Biophys Res Commun*, 255: 386-393).

SUMMARY OF THE INVENTION

This invention provides novel prostate cancer targeting mAbs that bind to components of the tumor specific internalizing epitope space. By using a library designed to trigger receptor endocytosis, and devising selections to eliminate cross reactive mAbs, a panel of 93 CaP specific mAbs were generated without prior knowledge of their target antigens. Over seventy of those mAbs recognize hormone refractory prostate cancer cells. All mAbs examined were efficiently endocytosed by CaP cell lines and thus can be used for efficient delivery of anti-tumor drugs to the cytosol. In addition, a number of the mAbs possess intrinsic anti-proliferative activity and have therapeutic utility as "naked" mAbs.

In certain embodiments, this invention provides an antibody that specifically binds to, and is internalized into, a prostate cancer cell. The antibody typically comprises an antibody that specifically binds an epitope that is specifically bound by bound an antibody selected from the group consisting of A33 (SEQ ID NO:22), M10A12 (SEQ ID NO:23), M9E4 (SEQ ID NO:24), OA12 (SEQ ID NO:25), M11G12 (SEQ ID NO:26), M11F12 (SEQ ID NO:27), and C10 (SEQ ID NO:28). In certain embodiments the antibody comprises at least one, at least two, at least three, at least four, at least five, or at least six CDRs found in Table 1 and/or Table 2. In certain embodiments the antibody comprises a VH region comprising at least one, at least two, or at least three CDRs found in Table 1. In certain embodiments the antibody comprises a VL region comprising at least one, at least two, or at least three CDRs found in Table 2. In certain embodiments VH region found in Table 1 and/or a VL VL region found in Table 2. In certain embodiments the antibody comprises a sequence selected from the group consisting of SEQ ID NO:2, SEQ ID NO 3, SEQ ID NO 4, SEQ ID NO 5, SEQ ID NO 6, SEQ ID NO 7, SEQ ID NO 8, SEQ ID NO:9, SEQ ID NO:10, SEQ ID NO:11, SEQ ID NO:12, SEQ ID NO:13, SEQ ID NO:14, SEQ ID NO:15, and conservative substitutions thereof. In certain embodiments the antibody comprises a sequence selected from the group consisting of SEQ ID NO:2, SEQ ID NO 3, SEQ ID NO 4, SEQ ID NO 5, SEQ ID NO 6, SEQ ID NO 7, and SEQ ID NO 8 attached to a sequence selected from the group consisting of SEQ ID NO:9, SEQ ID NO:10, SEQ ID NO:11, SEQ ID NO:12, SEQ ID NO:13, SEQ ID NO:14, SEQ ID NO:15. In certain embodiments the antibody consists of a single chain human antibody selected from the group consisting of A33 (SEQ ID NO:22), M10A12 (SEQ ID NO:23), M9E4 (SEQ ID NO:24), OA12 (SEQ ID NO:25), M11G12 (SEQ ID NO:26), M11F12 (SEQ ID NO:27), and/or C10 (SEQ ID NO:28). In various embodiments the antibody is a single chain antibody. In various embodiments the antibody is a Fab, a (Fab')2, an scFv, or an (ScFv')$_2$. In certain embodiments the antibody comprises a diabody.

In certain embodiments this invention provides a chimeric molecule molecule comprising an effector attached to an antibody described herein. Certain effectors include, but are not limited to an epitope tag, a second antibody, a label, a cytotoxin, a liposome, a radionuclide, a drug, a prodrug, a viral particle, a cytokine, a chelate, and the like. In certain embodiments the effector is an epitope tag selected from the group consisting of an avidin, and a biotin. In certain embodiments the effector is a cytotoxin selected from the group consisting of a Diphtheria toxin, a *Pseudomonas* exotoxin, a ricin, an abrin, and a thymidine kinase. In certain embodiments the effector is a chelate comprising a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

In certain embodiments the effector is a chelate comprising an alpha emitter (e.g., bismuth 213). In certain embodiments the effector is a chelate comprising DOTA. In certain embodiments the effector is a lipid or a liposome.

Also provided is a pharmaceutical formulation said formulation comprising: a pharmaceutically acceptable excipient and antibody and/or a chimeric molecule described herein. In certain embodiments the pharmaceutical formulation is a unit dosage formulation.

This invention also provides a method of inhibiting the growth or proliferation of a prostate cancer cell. The method typically involves contacting the cell with an antibody described herein. In various embodiments the cell is a metastatic cell and/or a solid tumor cell.

Also provided is a method of inhibiting the growth or proliferation of a prostate cancer cell where the method involves contacting the cell with chimeric molecule comprising an antibody described herein attached to a cytotoxic effector (e.g., a cytotoxin, a radionuclide, or liposome containing an anti-cancer drug, etc.). In various embodiments the cell is a metastatic and/or a solid tumor cell.

In various embodiments this invention provides a method of detecting a prostate cancer cell. The method typically involves contacting the prostate cancer cell with a chimeric molecule comprising an antibody described herein attached to a detectable label; and detecting the presence or absence or location of the detectable label. In various embodiments the detectable label is a selected from the group consisting of a gamma-emitter, a positron-emitter, an x-ray emitter, an alpha emitter, and a fluorescence-emitter.

This invention also provides another method of detecting a prostate cancer cell. This method typically involves contacting a prostate cancer cell with a chimeric molecule comprising an antibody described herein attached to an epitope tag; contacting the chimeric molecule with a chelate comprising a detectable moiety whereby the chelate binds to said epitope tag thereby associating said detectable moiety with said chelate; and detecting the detectable moiety. In various embodiments the detectable moiety is a radionuclide (e.g., a gamma-emitter, a positron-emitter, an alpha emitter, an x-ray emitter, etc.) and/or a fluorescence-emitter. In various embodiments detecting comprises external imaging and/or internal imaging. In certain embodiments the detectable moiety comprises a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and/or $^{111}$Ag. In certain embodiments the chelate comprises DOTA. In certain embodiments the epitope tag is an avidin or a biotin.

In certain embodiments this invention provides a nucleic acid comprising sequence that encodes an antibody described herein. In various embodiments this invention provides an expression vector comprising a nucleic acid sequence that encodes an antibody described herein. Also provided are cells containing the expression vector.

Kits are also provided. The kits typically comprise a container containing one or more antibodies described herein. In certain embodiments the kits further comprise an effector. In certain embodiments the effector is coupled to the antibody, while in other embodiments, the effector is in a container separate from the antibody. In various embodiments the effector comprises a chelate and/or a detectable label. In various embodiments antibody is in a pharmacologically acceptable excipient, preferably a sterile excipient.

DEFINITIONS

The term "epitope space" refers to the complete set of antigenic determinants (epitopes) recognizable by an ideal, naïve phage antibody library. Operationally, the size of this space is a function of experimental details, such as the size and quality of the library, selection methods, and the cell biology involved in handling cells of interest.

The term "tumor epitope space" refers to the complete set of tumor-specific or tumor-associated epitopes on a particular tumor specimen or tumor cell lines, recognizable by an ideal, naïve phage antibody library. Operationally, the size of this space is a function of experimental details, such as the size and quality of the library, the success of pre-adsorption against a corresponding normal cell line, selection methods, and the cell biology involved in handling tumor cells or cell lines of interest.

An "A33 antibody" refers to an internalizing antibody that specifically binds to an epitope that is specifically bound by the human A33 single-chain antibody described herein. The term "A33" antibody can also refer to the particular human A33 single-chain antibody whose sequence is provided herein. Similar usage applies to the terms an M10A12 antibody, a M9E4 antibody, an OA12 antibody, an M11G12 antibody, an M10F12 antibody, and a C10 antibody.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev. pp*169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "biotin" refers to biotin and modified biotins or biotin analogues that are capable of binding avidin or various avidin analogues. "Biotin", can be, inter alia, modified by the addition of one or more addends, usually through its free carboxyl residue. Useful biotin derivatives include, but are not limited to, active esters, amines, hydrazides and thiol groups that are coupled with a complimentary reactive group such as an amine, an acyl or alkyl group, a carbonyl group, an alkyl halide or a Michael-type acceptor on the appended compound or polymer.

Avidin, typically found in egg whites, has a very high binding affinity for biotin, which is a B-complex vitamin (Wilcheck et al. (1988) *Anal. Biochem*, 171: 1). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention. Both avidin and streptavidin have a tetravalency for biotin, thus permitting amplification when the former bind to biotin. In certain embodiments, four detection or therapeutic agents, such as nuclides, can be attached to each targeting protein.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H1$ by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$—$V_L$ heterodimer which may be expressed from a nucleic acid including $V_H$- and $V_L$-encoding sequences either joined directly or joined by a peptide-encoding linker. Huston, et al.

(1988) *Proc. Nat. Acad. Sci. USA,* 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

An "effector" refers to any molecule or combination of molecules whose activity it is desired to deliver/into and/or localize at cell. Effectors include, but are not limited to labels, cytotoxins, enzymes, growth factors, transcription factors, drugs, etc.

A "reporter" is an effector that provides a detectable signal (e.g. is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein, and used refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g. ligands bound by receptors), ligands bound by other ligands to form heterodimers or homodimers, $His_6$ bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:1) epitope, c-myc antibodies (available from Sigma, St. Louis), the HNK-1 carbohydrate epitope, the HA epitope, the HSV epitope, the $His_4$, $His_5$, and $His_6$ epitopes that are recognized by the His epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

BRIEF DESCRIPTION OF THE DRAWINGS

FIGS. 1A and 1B illustrate sequences of representative internalizing antibodies. Linker joining $V_H$ and $V_L$ domains is underlined.

FIG. 2A: Selection scheme: A naïve human phage antibody library was depleted on normal cells and subsequently incubated with prostate cancer cells at 37° C. to induce receptor mediated endocytosis. FIG. 2B: Comparative cell ELISA: Supernatants containing monoclonal phage antibody were incubated with PC3 and BPH-1 cells in parallel to reveal differential binding. FIG. 2C: Binding specificity determined by flow cytometry: Phage antibody A12 was incubated with prostate cancer (PC3 and DU-145) and control cells and bound phage detected by FITC conjugated anti-M13 antibodies. Filled peak: control, an irrelevant, hapten-binding phage mAb. Unfilled peak: CaP-specific phage mAb. FIG. 2D: Binding specificity determined by two color FACS analysis of mixed cell populations: RWPE-1 (control) cells were FITC-labeled, mixed with unlabeled PC3 cells and incubated with phage antibodies that bind to prostate cancer (M9E4, M10A12, and M11G12). Control: helper phage only. H3: pan cell binding antibody. Binding of erbB2 phage antibody F5 is shown as a reference.

FIG. 3A shows time course of phage antibody internalization by PC3 cells: The percentage of internalized phage is calculated as a fraction of the total phage bound and plotted as a function of time. Circle: M9E4 phage antibody; Square: A33 phage antibody; Diamond: M10A12 phage antibody. Insert: Internalized phage visualized by fluorescent microscopy. FIG. 3B shows ScFv-directed liposome endocytosis by prostate cancer cells: Fluorescent dye containing immunoliposomes (ILs) were constructed from six scFv which bound PC3 cells but not non-cancerous BPH-1 cells. After removal of surface bound ILs, internalized liposomes were quantified by fluorescence at 404 nm. Ctr: control, Ni-NTA liposome containing HPTS but without scFv coating. The ratio of sample reading over control was shown for comparison between PC3 and BPH-1 cells. FIG. 3 C shows direct observation of liposome HPTS uptake by PC3 cells using fluorescent microscopy. The result is shown for PC3 with A33 scFv (clone #1 in FIG. 3B). Control: liposome containing HPTS but without scFv coating.

DETAILED DESCRIPTION

Figure 2A:
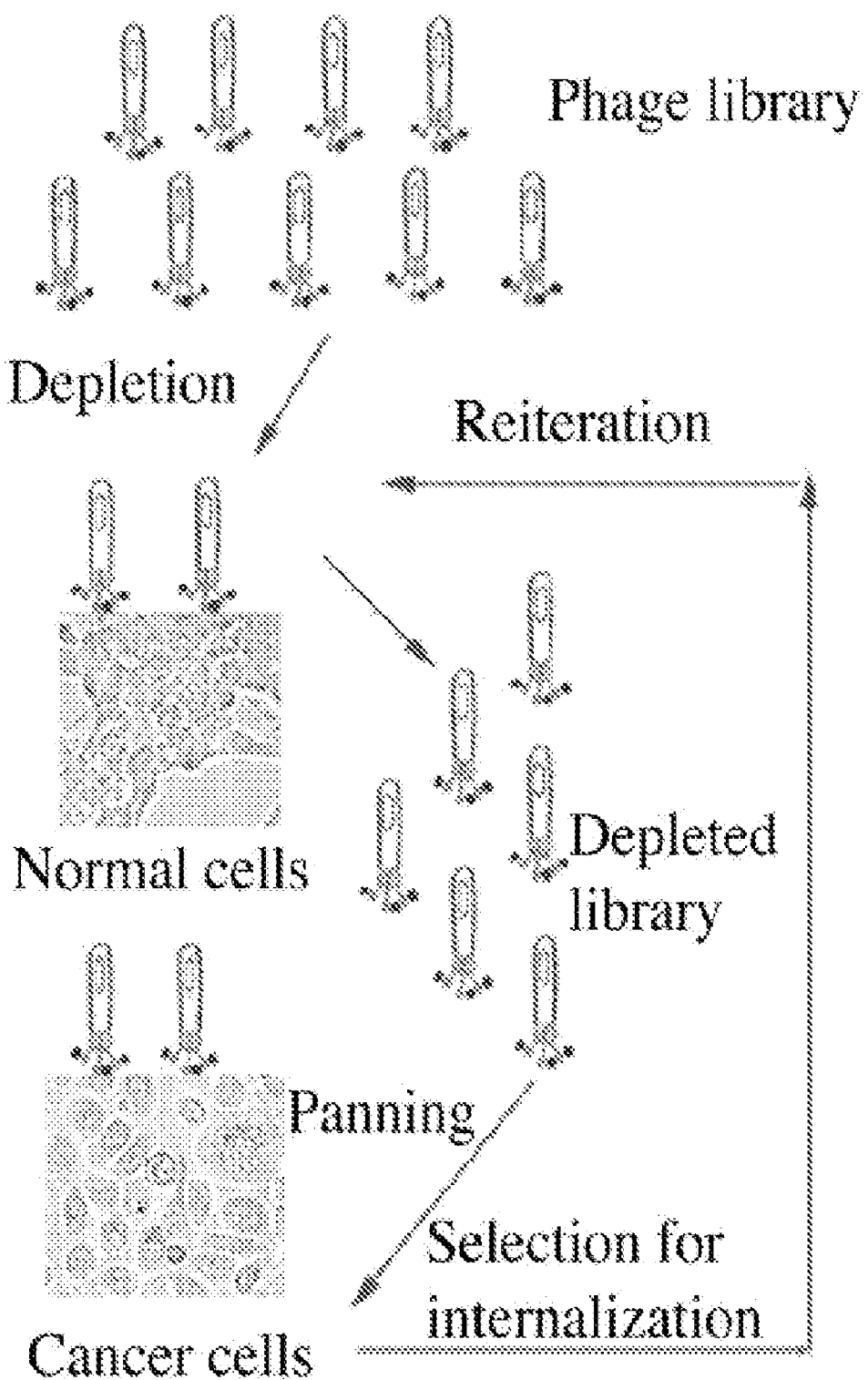
FIGS. 2A through 2D illustrate subtractive selection of CaP-specific internalizing antibody.

The identification of tumor-specific cell surface antigens is an important step towards the development of targeted therapeutics for cancer. The epitope space at the tumor cell surface is highly complex, composed of proteins, carbohydrate and other membrane-associated determinants including post-translational modification products, that are difficult to probe by approaches based on gene expression.

By selecting human antibody gene diversity libraries directly on the surface of prostate cancer cells, we have taken a functional approach to identifying fully human tumor-specific monoclonal antibodies. Selection conditions were optimized to favor tumor-specific antibody binding and internalization. Over ninety monoclonal antibodies were identified that specifically bind and enter prostate cancer cells, with little or no binding to control cells. These antibodies are able to efficiently deliver intracellular payloads when attached to effectors (e.g. various nanoparticles, liposomes, etc.). In addition, a number of the antibodies display intrinsic antiproliferative activity. The tumor-specific internalizing antibodies of this invention are useful for targeted therapeutics and/or imaging reagents either alone or in combination with effector molecules. The antigens they bind constitute a tumor specific internalizing epitope space which is likely to play a significant role in cancer cell homeostasis. Targeting components of this epitope facilitates development of immunotherapeutic and small molecule-based strategies, and also the utilization of other therapeutic agents that rely upon delivery to the interior of the tumor cell.

I. Internalizing Prostate Specific Antibodies.

This invention provides a number of antibodies that specifically bind and are internalized into human prostate cancer cells. The antibodies were identified by selecting human antibody gene diversity libraries directly on the surface of prostate cancer cells. Antibodies were identified that specifically bind and enter prostate cancer cells, with little or no binding to control cells.

For the selection process, the antibodies in the library were expressed as single chain Fv (scFv) antibodies comprising a variable heavy ($V_H$) region linked to a variable light ($V_L$) region by a peptide linker.

Representative antibodies (e.g. $V_H$ and $V_L$ domains) are illustrated in Tables 1 and 2, respectively.

TABLE 1

Amino acid sequences of variable heavy ($V_H$) region of illustrative anti-prostate cancer antibodies.

| Antibody | Framework 1 | CDR1 | Framework 2 | CDR2 | Framework 3 | CDR3 | Framework 4 | SEQ ID NO |
|---|---|---|---|---|---|---|---|---|
| A33 | QVQLQQS GGGLVQP GRSLRLS CAASGFA FD | DYA MH | WVRQAP GKGLEW VS | GISW NSGSI GYAD SVKG | RFTISRDN AKNSLYL QMNSLRA EDTALYY CAK | AQGS SWYY YGM DV | WGQGTM VTVSS | 2 |
| M10A12 | QVQLVES GGGVVQP GRSLRLS CTASGFT FS | SYGM H | WVRQAP GKGLEW VA | VISY DGSN KYYA DSVK G | RFTISRDN SKNTLYL QMNSLRA EDTAVYY CAR | GGRY SSNW FSYY YYG MDV | WGQGTTV TVSS | 3 |
| M9E4 | QVQLQQS GGGLVQP GRSLRLS CAASGFT FD | DYA MH | WVRQAP GKGLEW VS | GISW NSGSI GYAD SVKG | RFTISRDN AKNSLYL QMNSLRV EDTAVYY CAR | DNW GSID Y | WGQGTLV TVSS | 4 |
| OA12 | QVQLQES GGGVVQP GRSLRLS CAASGFT FS | SYDM H | WVRQAP GKGLEW VA | VIWY DGSN KYYA DSVK G | RFTISRDN SKNTLYL QMNSLRA EDTAVYY CAR | DRYG DYLF DY | WGQGTLV TVSS | 5 |
| M11G12 | QVQLQES GGGLVQP GGSLRLS CAASGFT FS | SYAM S | WVRQAP GKGLEW VS | AISGS GGST YYAD SVKG | RFTISRDN SKNTLYL QMSSLRA EDTAFYY CAN | SAYT GGW YDY | WGHGTLV TVSS | 6 |
| M11F12 | QVQLVQS GGGLVQP GGSLRLS CAASGFT VS | SNYM S | WVRQAP GKGLEW VS | VISGT GGST YYAD SVKG | RFTISRDN SKNTVYL QMNSLRA EDTAVYY CAR | ENWF LDY | WGQGALV TVSS | 7 |
| C10 | QVQLVES GGGLVKP GGSLRLS CAASGFT FS | SYAM H | WVRQAP GKGLEW VA | VISY DGSN KYYA DSVK G | RFTISRDN SKNTLYL QMNSLRA EDTAVYF CVR | PSDS GWSF EH | WGQGTLV PVSS | 8 |

The variable heavy regions in the A33 antibody are identified by amino acid sequences in Table 1 above are: Framework 1:residues 1-30 of SEQ ID NO:2, CDR1:residues 31-35 of SEQ ID NO:2, Framework 2:residues 36-49 SEQ ID NO:2, CDR2 residues 50-66 of SEQ ID NO:2, Framework 3:residues 67-98 of SEQ ID NO:2, CDR3::residues 99-111 of SEQ ID NO:2, and Framework 4:residues 112-122 of SEQ ID NO:2. The variable heavy regions in the M10A12 antibody are identified by amino acid sequences in Table 1 above are: Framework 1:residues 1-30 of SEQ TD NO:3, CDR1:residues 31-35 of SEQ ID NO:3, Framework 2:residues 36-49 SEQ ID NO:3, CDR2 residues 50-66 of SEQ TD NO:3, Framework 3:residues 67-98 of SEQ ID NO:3, CDR3:residues 99-116 of SEQ ID NO:3, and Framework 4:residues 117-127 of SEQ ID NO:3. The variable heavy regions in the M9E4 antibody are identified by amino acid sequences in Table 1 above are: Framework 1:residues 1-30 of SEQ ID NO:4, CDR1:residues 31-35 of SEQ ID NO:4, Framework 2:residues 36-49 SEQ ID NO:4, CDR2 residues 50-66 of SEQ ID NO:4, Framework 3:residues 67-98 of SEQ ID NO:4, CDR3:residues 99-106 of SEQ ID NO:4, and Framework 4:residues 107-117 of SEQ ID NO:4. The variable heavy regions in the OA12 antibody are identified by amino acid sequences in Table 1 above are: Framework 1:residues 1-30 of SEQ ID NO:5, CDR1:residues 31-35 of SEQ ID NO:5, Framework 2:residues 36-49 SEQ ID NO:5, CDR2 residues 50-66 of SEQ ID NO:5, Framework 3:residues 67-98 of SEQ ID NO:5, CDR3:residues 99-108 of SEQ TD NO:5, and Framework 4:residues 109-119 of SEQ ID NO:5. The variable heavy regions in the OA12 antibody are identified by amino acid sequences in Table 1 above are: Framework 1:residues 1-30 of SEQ ID NO:6, CDR1:residues 31-35 of SEQ ID NO:6, Framework 2:residues 36-49 SEQ ID NO:6, CDR2 residues 50-66 of SEQ ID NO:6, Framework 3:residues 67-98 of SEQ ID NO:6, CDR3:residues 99-108 of SEQ ID NO:6, and Framework 4:residues 109-119 of SEQ ID NO:6. The variable heavy regions in the M11F12 antibody are identified by amino acid sequences in Table 1 above are: Framework 1:residues 1-30 of SEQ TD NO:7, CDR1:residues 31-35 of SEQ ID NO:7, Framework 2:residues 36-49 SEQ ID NO:7, CDR2 residues 50-66 of SEQ ID NO:7, Framework 3:residues 67-98 of SEQ ID NO:7, CDR3:residues 99-105 of SEQ ID NO:7, and Framework 4:residues 106-116 of SEQ ID NO:7. The variable heavy regions in the C10 antibody are identified by amino acid sequences in Table 1 above are: Framework 1:residues 1-30 of SEQ ID NO:8, CDR1:residues 31-35 of SEQ ID NO:8, Framework 2:residues 36-49 SEQ ID NO:8, CDR2 residues 50-66 of SEQ ID NO:8, Framework 3:residues 67-98 of SEQ ID NO:8, CDR3: residues 99-108 of SEQ ID NO:8, and Framework 4:residues 109-119 of SEQ ID NO:8.

TABLE 2

Amino acid sequences of variable light (V$_L$) region of illustrative anti-prostate cancer antibodies.

| Antibody | Framework 1 | CDR1 | Framework 2 | CDR2 | Framework 3 | CDR3 | Framework 4 | SEQ ID NO |
|---|---|---|---|---|---|---|---|---|
| A33 | DVVMTQ DPAVSVA LGQTVRI TC | QGDSL RSYYA S | WYQQKP GQAPVL VI | YGKN NRPS | GIPDRFSG SSSGNTAS LTITGAQA EDEADYY C | NSRD SSGN PWV | FGGGTKL TVL | 9 |
| M10A12 | SSELTQD PAVSVAL GQTVRIT C | QGDSL RSYYA S | WYQQKP GQAPLLV I | YGEN NRPS | GIPDRFSG SSSGNTAF LTISRVEA GDEADYY C | QVW DSSS DHPG VV | FGGGTKV TVL | 10 |
| M9E4 | SSELTQD PAVSVAL GQTVRIT C | QGDSL RNYFV S | WFQKKP GQAPVL VV | YDDT DRPS | GIPERFSG SNSGNTA TLTISRIEA GDEADYY C | QLW DTGS DHAV V | FGGGTKL TVL | 11 |
| OA12 | QSVLTQP PSVSGAP GQRVTIS C | TGRSSN IGAGY DIH | WYQHLP GTAPKLL I | YGNS NRPS | GVPDRFS GSKSGTSA SLAISGLQ SEDEADY YC | AAW DDSL NAVV | FGGGTKV TVL | 12 |
| M11G12 | SSELTQD PAVSVAL GQTVKIT C | QGDSL RTYYA S | WYQQRP GQAPVL VI | YGEN SRPS | GIPDRFSG SSSGNTAS LTITGAQA EDEADYY C | NSRD SSGN HLRV | FGGGTKL TVL | 13 |
| M11F12 | QSALTQD PAVSVAL GQTVRIT C | RGDSL GTYYA T | WYQQKP GQAPVL VI | YGEN NRPS | GIPDRFSG SSSGNTAS LTITGAQA EDEADYY C | NSRD SSGN HVV | FGRGTKL TVL | 14 |
| C10 | SSELTQD PAVSVAL GQTVRIT C | QGDSL RSYYA S | WYQQKP GQAPVL VI | YGKN NRPS | GIPDRFSG SSSGNTAS LTITGAQA EDEADYY C | NSRD SSGN RNW V | FGGGTKL AVL | 15 | of SEQ ID NO:5, CDR1:residues 31-35 of SEQ ID NO:5, Framework 2:residues 36-49 SEQ ID NO:5, CDR2 residues 50-66 of SEQ ID NO:5, Framework 3:residues 67-98 of SEQ The variable light regions in the A33 antibody are identified by amino acid sequences in Table 2 above are: Framework 1:residues 1-22 of SEQ ID NO:9, CDR1:residues 23-33 of SEQ ID NO:9 Framework 2:residues 34-47 SEQ ID NO:9, CDR2 residues 48-55 of SEQ ID No:9,Framework 3:residues 56-87 of SEQ ID NO:9, CDR3: residues 88-98 of SEQ ID NO:9, and Framework 4:residues 98-108 of SEQ ID NO:9. The variable light regions in the M10A12 antibody are identified by amino acid sequences in Table 2 above are: Framework 1:residues 1-22 of SEQ ID NO:10, CDR1:residues 23-33 of SEQ ID NO:10, Framework 2:residues 34-47 SEQ ID NO:10, CDR2 residues 48-55 of SEQ TD NO:10, Framework 3:residues 56-87 of SEQ ID NO:10, CDR3: residues 88-100 of SEQ ID NO:10, and Framework 4:residues 101-110 of SEQ ID NO:10. The variable light regions in the M9E4 antibody are identified by amino acid sequences in Table 2 above are: Framework 1:residues 1-22 of SEQ ID NO:11, CDR1:residues 23-33 of SEQ ID NO:11, Framework 2:residues 34-47 SEQ ID NO:11, CDR2 residues 48-55 of SEQ ID NO:11, Framework 3:residues 56-87 of SEQ ID NO:11, CDR3: residues 88-99 of SEQ ID NO:11, and Framework 4:residues 100-109 of SEQ ID NO: 11. The variable heavy regions in the OA12 antibody are identified by amino acid sequences in Table 2 above are: Framework 1:residues 1-22 of SEQ ID NO:12, CDR1:residues 23-33 of SEQ ID NO:12, Framework 2:residues 34-47 SEQ ID NO:12, CDR2 residues 48-55 of SEQ ID NO:12, Framework 3:residues 56-87 of SEQ ID NO:12, CDR3: residues 88-98 of SEQ ID NO:12, and Framework 4:residues 99-108 of SEQ ID NO:12. The variable light regions in the M 11G12 antibody are identified by amino acid sequences in Table 2 above are: Framework 1:residues 1-22 of SEQ ID NO:13, CDR1:residues 23-33 of SEQ ID NO:13, Framework 2:residues 34-47 SEQ ID NO:13, CDR2 residues 48-55 of SEQ ID NO:13, Framework 3:residues 56-87 of SEQ ID NO:13, CDR3: residues 88-99 of SEQ ID NO:13, and Framework 4:residues 100-109 of SEQ ID NO: 13. The variable light regions in the M11F12 antibody are identified by amino acid sequences in Table 2 above are: Framework 1:residues 1-22 of SEQ ID NO:14, CDR1:residues 23-33 of SEQ ID NO:14, Framework 2:residues 34-47 SEQ ID NO:14, CDR2 residues 48-55 of SEQ ID NO:14, Framework 3:residues 56-87 of SEQ ID NO:14, CDR3: residues 88-98 of SEQ ID NO:14, and Framework 4:residues 99-108 of SEQ ID NO: 14. The variable light regions in the C10 antibody are identified by amino acid sequences in Table 2 above are: Framework 1:residues 1-22 of SEQ ID NO:15, CDR1:residues 23-33 of SEQ ID NO:15, Framework 2:residues 34-47 SEQ ID NO:15, CDR2 residues 48-55 of SEQ TD NO:15, Framework 3:residues 56-87 of SEQ ID NO:15, CDR3:residues 88-99 of SEQ ID NO:15, and Framework 4:residues 100-109 of SEQ ID NO:15.

In certain embodiments, for single chain Fv antibodies the variable heavy (VH) region is coupled to the Variable light ($V_L$) either directly, or more preferably by a peptide linker (e.g. $(Gly_4Ser)_3$, SEQ ID NO:16).

Using the sequence information provided in Tables 1 and 2, the antibodies listed therein (e.g., A33 (SEQ ID NO:22), M10A12 (SEQ ID NO:23), M9E4 (SEQ ID NO:24), OA12 (SEQ ID NO:25), M11G12 (SEQ ID NO:26), M11F12 (SEQ ID NO:27), C10 (SEQ ID NO:28), etc.) can readily be prepared using standard methods (e.g. chemical synthesis methods and/or recombinant expression methods) well known to those of skill in the art.

In addition, other "related" prostate cancer specific antibodies can be identified by screening for antibodies that bind to the same epitope (e.g. that compete with the listed antibodies for binding to a prostate cancer cell) and/or by modification of the antibodies identified herein (e.g., A33, M10A12, M9E4, OA12, M11G12, M11F12, C10) to produce libraries of modified antibody and then rescreening antibodies in the library for improved binding to prostate cancer cells, and/or by screening of various libraries on prostate cancer cells as illustrated in Example 1.

A) Chemical Synthesis.

Using the sequence information provided herein, the prostate cancer specific antibodies of this invention (e.g., A33, M10A12, M9E4, OA12, M11G12, M11F12, C10), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3-284 in *The Peptides: Analysis, Synthesis, Biology*. Vol. 2: *Special Methods in Peptide Synthesis*, Part A., Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

B) Recombinant Expression of Prostate Cancer-Specific Antibodies.

In certain preferred embodiments, the prostate cancer specific antibodies of this invention (e.g., A33, M10A12, M9E4, OA12, M11G12, M11F12, C10), or variants thereof, are prepared using standard techniques well known to those of skill in the art. Using the sequence information provided herein, nucleic acids encoding the desired antibody can be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159-6168) or manually synthesized using the solid phase phosphoramidite triester method described by Beaucage et. al. (Beaucage et. al. (1981) *Tetrahedron Letts.* 22(20): 1859-1862). Alternatively, nucleic acids encoding the antibody can be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl. Acad. Sci. USA* 86: 10029-10033. In addition, detailed protocols for the expression of the antibodies of this invention are provided herein in the Examples.

C) Identification of Other Antibodies Binding the Same Epitope(s) as Antibodies A33, M10A12, M9E4, OA12, M11G12, M11F12, and/or C10

Having identified useful prostate cancer specific internalizing antibodies (e.g., A33, M10A12, M9E4, OA12, M11G12, M11F12, C10), other "related" internalizing prostate cancer specific antibodies can be identified by screening for antibodies that cross-react with the identified antibodies, either at the epitope bound by the antibodies, and/or for antibodies that cross-react with the identified antibodies for binding to a prostate cancer cell (e.g., CaP cells, PC3 cells, etc.), and/or with an idiotypic antibody raised against the A33, M10A12, M9E4, OA12, M11G12, M11F12, and/or C10 antibodies of this invention.

1) Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. One generally preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-Reactivity with the A33, M10A12, M9E4, OA12, M11G12, M11F12, and/or C10 Antibodies of this Invention.

In another approach, other prostate cancer specific antibodies of this invention can be identified by the fact that they bind the same epitope as the "prototypic" antibodies of this invention (e.g., A33, M10A12, M9E4, OA12, M11G12, M11F12, C10, etc.). To identify such antibodies, it s not necessary to isolate the subject epitope. In certain embodiments, one can screen, e.g. antibody libraries for antibodies that compete with the prototypic antibodies of this invention for binding and/or internalization by a prostate cancer cell (e.g. a CaP cell, a PC3 cell, etc.).

Methods of screening libraries for cell binding and/or internalization are described in detail in the examples. Such screening methods, done, for example in the presence of labeled prototypic antibodies of this invention allows rapid identification of library members that compete with and exclude the prototypic antibodies of this invention from binding and/or internalization into the target prostate cancer cell.

In addition, it is noted that methods of determining antibody cross-reactivity are well known to those of skill in the art. Generally the epitope bound by the prototypic antibodies of this invention is determined e.g. by epitope mapping techniques. Methods of epitope mapping are well known to those of skill in the art (see, e.g., Reyes et al. (1992) *Hepatitis E Virus (HEV): Epitope Mapping and Detection of Strain Variation*, Elsevier Science Publisher Shikata et al. eds., Chapter 43:237-245; Li et al. (1993) *Nature* 363: 85-88). Epitope mapping can be performed using Novatope system, a kit for which is commercially available from Novagen, Inc.

In certain embodiments, cross-reactive prostate cancer specific antibodies show at least 60%, preferably 80%, more preferably 90%, and most preferably at least 95% or at least 99% cross-reactivity with one or more of the prototypic antibodies of this invention.

D) Phage Display Methods to Select Other "Related" Prostate Cancer Specific Antibodies.

1) Chain Shuffling Methods.

One approach to creating modified single-chain antibody (scFv) gene repertoires has been to replace the original $V_H$ or $V_L$ gene with a repertoire of V-genes to create new partners (chain shuffling) (Clackson et al. (1991) *Nature*. 352: 624-628). Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779-783).

Thus, for example, to alter the affinity of a prostate cancer specific antibodies, a mutant scFv gene repertoire can be created containing a $V_H$ gene of the prototypic antibodies (e.g. as shown in Table 1) antibody and a human $V_L$ gene repertoire (light chain shuffling). The scFv gene repertoire can be cloned into a phage display vector, e.g., pHEN-1 (Hoogenboom et al. (1991) *Nucleic Acids Res.,* 19: 4133-4137) or other vectors, e.g. as described herein in the examples, and after transformation a library of transformants is obtained.

Similarly, for heavy chain shuffling, the prostate cancer specific antibody (e.g., A33, M10A12, M9E4, OA12, M11G12, M11F12, C10) $V_H$ CDR1 and/or CDR2, and/or CDR3 and light chain (see, e.g., Table 2) are cloned into a vector containing a human $V_H$ gene repertoire to create a phage antibody library transformants. For detailed descriptions of chain shuffling to increase antibody affinity see Schier et al. (1996) *J. Mol. Biol.,* 255: 28-43, 1996.

2) Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.,* 196: 901-917; Chothia et al. (1986) *Science,* 233: 755-8; Nhan et al. (1991) *J. Mol. Biol.,* 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.,* 234: 564-578; Wells (1990) *Biochemistry,* 29: 8509-8516). Site-directed mutagenesis of CDRs and screening against the prostate cancer cells, e.g. as described herein in the examples, can produce antibodies having improved binding affinity.

3) CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., A33, M10A12, M9E4, OA12, M11G12, M11F12, C10) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.,* 234: 564-578).

$V_H$ CDR3 often occupies the center of the binding pocket, and thus mutations in this region are likely to result in an increase in affinity (Clackson et al. (1995) *Science,* 267: 383-386). In one embodiment, four $V_H$ CDR3 residues are randomized at a time using the nucleotides NNS (see, e.g., Schier et al. (1996) *Gene,* 169: 147-155; Schier and Marks (1996) *Human Antibodies and Hybridomas.* 7: 97-105, 1996; and Schier et al. (1996) *J. Mol. Biol.* 263: 551-567, 1996).

E) Creation of Other Antibody Forms.

Using the known and/or identified sequences (e.g. $V_H$ and/or $V_L$ sequences) of the single chain antibodies provided herein other antibody forms can readily be created. Such forms include, but are not limited to multivalent antibodies, full antibodies, scFv, (scFv')$_2$, Fab, (Fab')$_2$, chimeric antibodies, and the like.

1) Creation of Homodimers.

For example, to create (scFv')$_2$ antibodies, two prostate cancer specific scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g. by BIAcore.

In one particularly preferred embodiment, the (scFv')$_2$ dimer is created by joining the scFv' fragments through a linker, more preferably through a peptide linker. This can be accomplished by a wide variety of means well known to those of skill in the art. For example, one preferred approach is described by Holliger et al. (1993) *Proc. Natl. Acad. Sci. USA,* 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$—$C_H$1 by a disulfide bond and can readily be created using standard methods known to those of skill in the art. The F(ab)'$_2$ can be produced by dimerizing the Fab, e.g. as described above for the (scFv')$_2$ dimer.

2) Chimeric Antibodies.

The antibodies of this invention also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein are fully human antibodies, chimeric antibodies are contemplated, particularly when such antibodies are to be used in species other than humans (e.g. in veterinary applications). Chimeric antibodies are antibodies comprising a portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643; and anti-tumor antigens: Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces a prostate cancer specific antibody of this invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of a prostate cancer specific antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

3) Intact Human Antibodies.

In another embodiment, this invention provides for intact, fully human prostate cancer specific antibodies. Such antibodies can readily be produced in a manner analogous to making chimeric human antibodies. In this instance, instead of using a recognition function derived, e.g. from a murine, the fully human recognition function (e.g., VH and $V_L$) of the antibodies described herein is utilized.

4) Diabodies.

In certain embodiments, this invention contemplates diabodies comprising one or more of the $V_H$ and $V_L$ domains described herein. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

5) Measurement of Antibody/Polypeptide Binding Affinity.

As explained above, selection for increased avidity can involves measuring the affinity of the antibody for the target antigen (e.g., a prostate cancer cell). Methods of making such measurements are well known to those of skill in the art. Briefly, for example, the $K_d$ of the antibody is determined from the kinetics of binding to, e.g. the target cell in a BIAcore, a biosensor based on surface plasmon resonance. For this technique, the antigen or cell is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

II. Libraries and Vectors.

In another embodiment, this invention provides libraries and vectors for practice of the methods described herein. The libraries include monovalent or polyvalent libraries, including diabody libraries and more preferably including multivalent single chain antibody libraries (e.g. scFv), (e.g., expressed by phage).

The libraries can take a number of forms. Thus, in one embodiment the library is a collection of cells containing members of the phage display library, while in another embodiment, the library consists of a collection of isolated phage, and in still another embodiment, the library consists of a library of nucleic acids encoding a polyvalent phage display library. In certain embodiment, the nucleic acids can be phagemid vectors encoding the antibodies and ready for subcloning into a phage vector or the nucleic acids can be a collection of phagemid already carrying the subcloned antibody-encoding nucleic acids.

III. Chimeric Moieties Comprising Anti-Prostate Cancer Antibodies.

The prostate cancer-specific antibodies of this invention specifically bind to and are internalized by prostate cancer cells. The antibodies can be used alone as therapeutics (e.g. to inhibit growth and/or proliferation of a prostate cancer cell) or they can be coupled to an effector to provide efficient and specific delivery of the effector (e.g. an effector molecule such as a cytotoxin, a radiolabel, etc.) to various prostate cancer cells (e.g. isolated cells, metastatic cells, solid tumor cells, etc.).

In preferred embodiments, the antibodies of this invention are utilized in a "pretargeting" strategy (resulting in formation of a chimeric moiety at the target site after administration of the effector moiety) or in a "targeting" strategy where the antibody is coupled to an effector molecule prior to use to provide a chimeric molecule.

A chimeric molecule or chimeric composition or chimeric moiety refers to a molecule or composition wherein two or more molecules that exist separately in their native state are joined together to form a single molecule having the desired functionality of its constituent molecules. Typically, one of the constituent molecules of a chimeric molecule is a "targeting molecule". The targeting molecule is a molecule such as a ligand or an antibody that specifically binds to its corresponding target, in this case a prostate cancer cell.

Another constituent of the chimeric molecule is an "effector". The effector molecule refers to a molecule or group of molecules that is to be specifically transported to the target cell (e.g., a prostate cancer cell). It is noted that in this context, such specific transport need not be exclusively to or into a cancer cell, but merely need to provide preferential delivery of the effector to or into the cancer cell as compared to normal healthy cells.

The effector molecule typically has a characteristic activity that is to be delivered to the target cell. Effector molecules include, but are not limited to cytotoxins, labels, radionuclides, ligands, antibodies, drugs, liposomes, nanoparticles, viral particles, cytokines, and the like.

In certain embodiments, the effector is a detectable label, with preferred detectable labels including radionuclides. Among the radionuclides and labels useful in the radionuclide-chelator—(e.g. biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting and prostate cancers in the body of a mammal. These methods typically involve administering to the mammal a composition comprising, in a quantity sufficient for detection by a detector (e.g. a gamma detecting probe), an prostate cancer specific antibody labeled with a detectable label (e.g. antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

The label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place.

In addition to detectable labels, preferred effectors include cytotoxins (e.g. *Pseudomonas* exotoxin, ricin, abrin, Diphtheria toxin, and the like), or cytotoxic drugs or prodrugs, in which case the chimeric molecule may act as a potent cell-killing agent specifically targeting the cytotoxin to prostate cancer cells.

In still other embodiments, the effector can include a liposome encapsulating a drug (e.g. an anti-cancer drug such as doxirubicin, vinblastine, taxol, etc.), an antigen that stimulates recognition of the bound cell by components of the immune system, an antibody that specifically binds immune system components and directs them to the prostate cancer and the like.

A) Certain Preferred Effectors.

1) Imaging Compositions.

In certain embodiments, the chimeric molecules of this invention can be used to direct detectable labels to a tumor site. This can facilitate tumor detection and/or localization. In certain particularly preferred embodiments, the effector component of the chimeric molecule is a "radioopaque" label, e.g. a label that can be easily visualized using x-rays. Radioopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,981, organobismuth composites (see, e.g., U.S. Pat. No. 5,256,334), radiopaque barium polymer complexes (see, e.g., U.S. Pat. No. 4,866,132), and the like.

The antibodies of this invention can be coupled directly to the radiopaque moiety or they can be attached to a "package" (e.g. a chelate, a liposome, a polymer microbead, etc.) carrying or containing the radiopaque material as described below.

In addition to radiopaque labels, other labels are also suitable for use in this invention. Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

2) Radiosensitizers.

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2, 4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Alpha Emitters.

In certain embodiments, the effector can include an alpha emitter, i.e. a radioactive isotope that emits alpha particles. Alpha-emitters have recently been shown to be effective in the treatment of cancer (see, e.g., McDevitt et al. (2001) *Science* 294:1537-1540; Ballangrud et al. (2001) *Cancer Res.* 61: 2008-2014; Borchardt et al. (2003) *Cancer Res.* 63: 5084-50). Suitable alpha emitters include, but are not limited to Bi, $^{213}$Bi, $^{211}$At, and the like.

4) Ligands.

The effector molecule can also be a ligand, an epitope tag, or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the prostate cancer cell(s).

5) Chelates

Many of the pharmaceuticals and/or radiolabels described herein are preferably provided as a chelate, particularly where a pre-targeting strategy is utilized. The chelating molecule is typically coupled to a molecule (e.g. biotin, avidin, streptavidin, etc.) that specifically binds an epitope tag attached to a prostate cancer specific antibody of this invention.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively, the chelating agent can be coupled, directly or through a linker, to an epitope tag or to a moiety that binds an epitope tag. Conjugates of DOTA and biotin have been described (see, e.g., Su (1995) *J. Nucl. Med.,* 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.,* 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

6) Cytotoxins.

The antibodies of this invention can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters as described above.

Enzymatically active toxins and fragments. thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example.

Particularly preferred cytotoxins include *Pseudomonas* exotoxins, Diphtheria toxins, ricin, and abrin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

Where the antibody is attached to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:17).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:18) (as in native PE), REDL (SEQ ID NO:19), RDEL (SEQ ID NO:20), or KDEL (SEQ ID NO:21), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308-312 and Seetharam et al, *J. Biol. Chem.* 266: 17376-17381. Preferred forms of PE comprise the PE molecule designated PE38QQR. (Debinski et al. *Bioconj. Chem.*, 5: 40 (1994)), and PE4E (see, e.g., Chaudhary et al. (1995) *J. Biol. Chem.*, 265: 16306).

Methods of cloning genes encoding PE fused to various ligands are well known to those of skill in the art (see, e.g., Siegall et al. (1989) *FASEB J.*, 3: 2647-2652; and Chaudhary et al. (1987) *Proc. Natl. Acad. Sci. USA*, 84: 4538-4542).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science*, 175: 901-903; Uchida et al. (1973) *J. Biol. Chem.*, 248: 3838-3844).

In a preferred embodiments, the antibody-Diphtheria toxin chimeric molecules of this invention have the native receptor-binding domain removed by truncation of the Diphtheria toxin B chain. Particularly preferred is DT388, a DT in which the carboxyl terminal sequence beginning at residue 389 is removed. Chaudhary et al. (1991) *Bioch. Biophys. Res. Comm.*, 180: 545-551. Like the PE chimeric cytotoxins, the DT molecules can be chemically conjugated to the prostate cancer specific antibody, but, in certain preferred embodiments, the antibody will be fused to the Diphtheria toxin by recombinant means (see, e.g., Williams et al. (1990) *J. Biol. Chem.* 265: 11885-11889).

7) Viral Particles.

In certain embodiments, the effector comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (prostate cancer) cell. The use of viral particles to deliver nucleic acids to cells is described in detail in WO 99/55720, U.S. Pat. No. 6,670,188, U.S. Pat. No. 6,642,051, and U.S. Pat. No. 6,669,936.

8) Other Therapeutic Moieties.

Other suitable effector molecules include pharmacological agents or encapsulation systems containing various pharmacological agents. Thus, the targeting molecule of the chimeric molecule can be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule can comprise an encapsulation system, such as a viral capsid, a liposome, or micelle that contains a therapeutic composition such as a drug, a nucleic acid (e.g. an antisense nucleic acid or another nucleic acid to be delivered to the cell), or another therapeutic moiety that is preferably shielded from direct exposure to the circulatory system. Means of preparing liposomes attached to antibodies are well known to those of skill in the art. See, for example, U.S. Pat. No. 4,957,735, Connor et al. (1985) *Pharm. Ther.*, 28: 341-365. In addition coupling of liposomes to antibodies of this invention is illustrated herein in the Examples.

B) Attachment of the Antibody to the Effector.

One of skill will appreciate that the antibodies of this invention and the effector molecule(s) can be joined together in any order. Thus, where antibody is a single chain polypeptide, the effector molecule can be joined to either the amino or carboxy termini of the targeting molecule. The targeting molecule can also be joined to an internal region of the effector molecule, or conversely, the effector molecule can be joined to an internal location of the targeting molecule, as long as the attachment does not interfere with the respective activities of the molecules.

The antibody and the effector can be attached by any of a number of means well known to those of skill in the art. Typically the effector is conjugated, either directly or through a linker (spacer), to the targeting molecule. However, In certain embodiments, where both the effector molecule and the antibody are polypeptides it is preferable to recombinantly express the chimeric molecule as a single-chain fusion protein.

1) Conjugation of the Effector Molecule to the Antibody.

In one embodiment, the prostate cancer specific antibody is chemically conjugated to the effector molecule (e.g., a cytotoxin, a label, a ligand, or a drug or liposome, etc.). Means of chemically conjugating molecules are well known to those of skill.

The procedure for attaching an effector to an antibody will vary according to the chemical structure of the effector and/or antibody. Polypeptides typically contain variety of functional groups; e.g., carboxylic acid (COOH) or free amine (—NH$_2$)

groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659, 839).

Many procedure and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann (1991) *Science,* 252: 1657, U.S. Pat. Nos. 4,545,985 and 4,894,443.

In some circumstances, it is desirable to free the effector from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient=s complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2 Conjugation of Chelates.

In certain preferred embodiments, the effector comprises a chelate that is attached to an antibody or to an epitope tag. The prostate cancer specific antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

3) Production of Fusion Proteins.

Where the antibody and/or the effector is relatively short (i.e., less than about 50 amino acids) they can be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.,* 85: 2149-2156 (1963), and Stewart et al., *Solid Phase Peptide Synthesis,* 2nd ed. Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In a preferred embodiment, DNA encoding fusion proteins of the present invention may be cloned using DNA amplification methods such as polymerase chain reaction (PCR). Thus, for example, the nucleic acid encoding a -prostate specific antibody of this invention is PCR amplified, using a sense primer containing the restriction site for NdeI and an antisense primer containing the restriction site for HindIII. This produces a nucleic acid encoding the antibody sequence and having terminal restriction sites. A PE38QQR fragment may be cut out of the plasmid pWDMH4-38QQR or plasmid pSGC242FdN1 described by Debinski et al. (1994) *Int. J. Cancer*, 58: 744-748. Ligation of the antibody and PE38QQR sequences and insertion into a vector produces a vector encoding the antibody joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules can be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

IV) Pharmaceutical Compositions.

The prostate cancer specific antibodies, and/or chelates, and/or chimeric molecules of this invention are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present antibodies and/or chimeric molecules (e.g. fusion proteins) or a cocktail thereof (i.e., with other proteins) can be administered for therapeutic treatments. In therapeutic applications, compositions are administered to a patient suffering from a disease, e.g., a cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream One of skill in the art will appreciate that in these instances, the therapeutic compositions of this invention can be administered directly to the tumor site. Thus, for example, prostate tumors can be treated by administering the therapeutic composition directly to the tumor site (e.g., through a surgically implanted catheter).

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

VIII. Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

Such a kit according to the present invention preferably comprises a prostate cancer specific antibody of this invention. The antibody can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the complex-forming reaction with the prostate cancer specific antibody can simply be produced by combining the components in a neutral medium and causing them to react. For that purpose the effector may be presented to the antibody in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Mapping Tumor Epitope Space by Direct Selection of Single Chain Fv Antibody Libraries on Prostate Cancer Cells The identification of tumor-specific cell surface antigens is a critical step towards the development of targeted therapeutics for cancer. The epitope space at the tumor cell surface is highly complex, composed of proteins, carbohydrate and other membrane-associated determinants including post-translational modification products, which are difficult to probe by approaches based on gene expression. This epitope space can be efficiently mapped by complementary monoclonal antibodies. By selecting human antibody gene diversity libraries directly on the surface of prostate cancer cells, we have taken a functional approach to identifying fully human tumor-specific monoclonal antibodies without prior knowledge of their target antigens. Selection conditions have been optimized to favor tumor-specific antibody binding and internalization. To date we have discovered over ninety monoclonal antibodies which specifically bind and enter prostate cancer cells, with little or no binding to control cells. These antibodies are able to efficiently deliver intracellular payloads when attached to nanoparticles such as liposomes. In addition, a subset of the antibodies displayed intrinsic antiproliferative activity. These tumor-specific internalizing antibodies are likely to be useful for targeted therapeutics either alone or in combination with effector molecules. The antigens they bind constitute a tumor specific internalizing epitope space which is likely to play a significant role in cancer cell homeostasis. Targeting components of this epitope space facilitates development of immunotherapeutic and small molecule-based strategies and also the utilization of other therapeutic agents that rely upon delivery to the interior of the tumor cell.

Results

Subtractive Selection for CaP-Specific Internalizing Phage Antibody

A non-immune, multivalent phage display library that contains more than 100 million different antibody variable fragments was used for subtractive cell selection. The phage display library were pre-absorbed against a panel of normal cell lines—including a normal, immortalized prostate epithelium line (RWPE-1), epithelial cells derived from benign prostatic hyperplasia glands (BPH-1) (Hayward et al. (1995) In Vitro Cell Dev Biol Anim, 31: 14-24), normal human fibroblasts, and normal breast epithelial lines (MCF10A and HMEC)—to remove those antibodies which bind to common cell surface molecules. The depleted antibody library was incubated with either one of two hormone refractory CaP lines (PC3 and DU-145) and one hormone sensitive line (LN-CaP) under conditions which allowed receptor-mediated endocytosis (FIG. 2A). Surface bound phage that failed to internalize were removed by a low pH glycine buffer washes and internalized phage were recovered by lysing the cells followed by amplifications in E. coli.

Figure 2B:
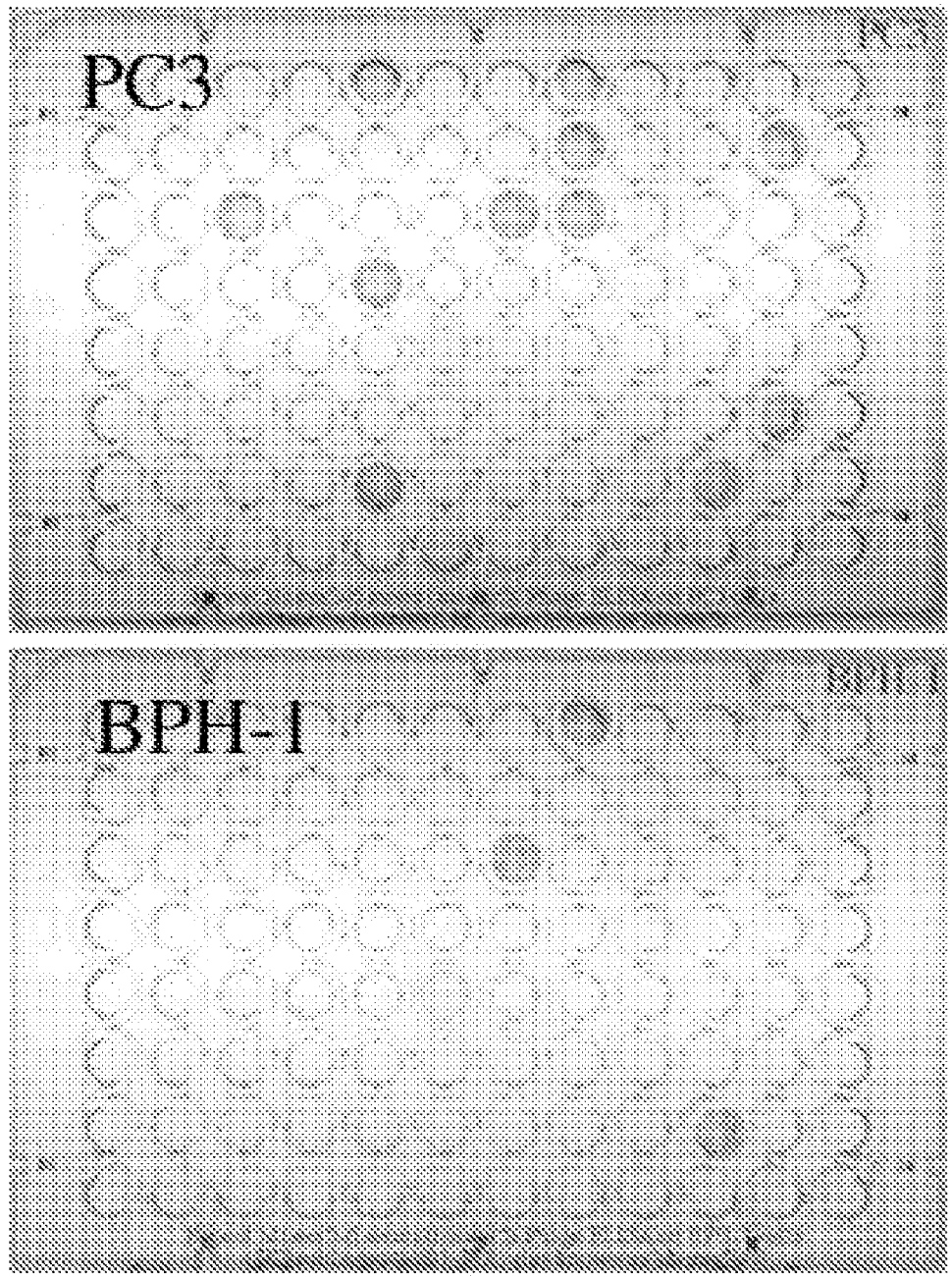
Figure 2C:
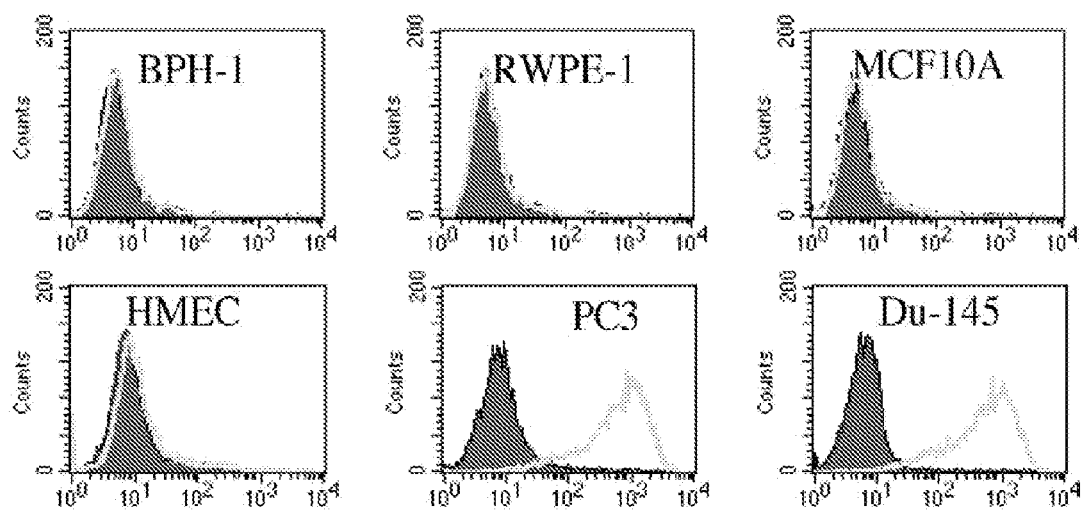
Figure 2D:
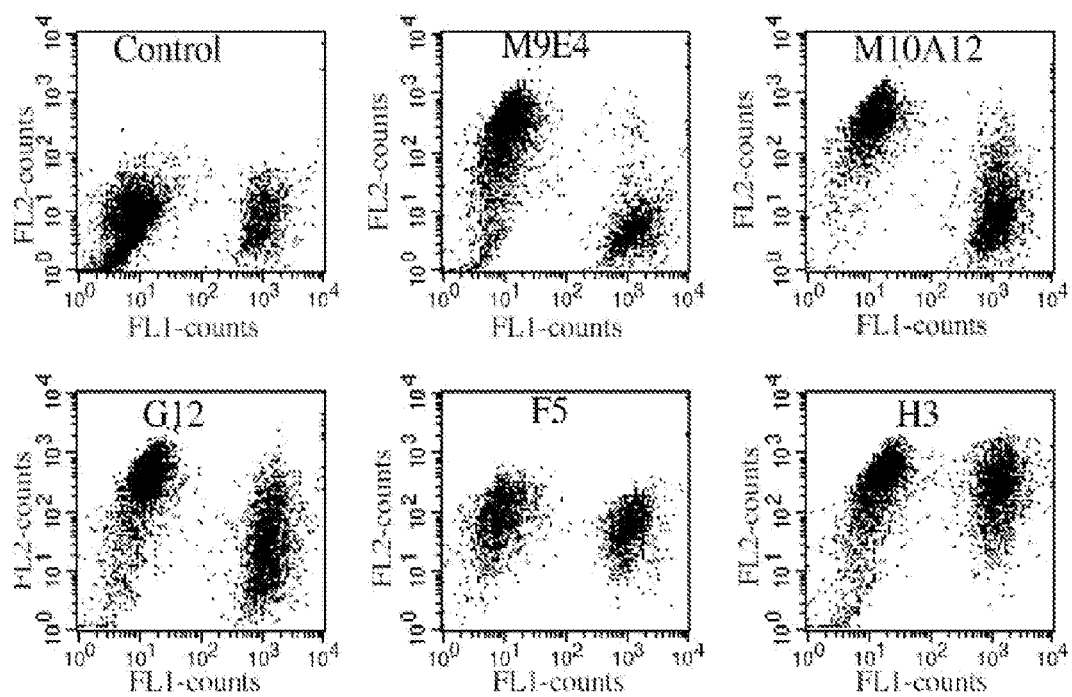

After two rounds of subtractive selection, 22% to 43% of the phage output bound the selecting cell line (Table 3) as determined by cell ELISA (FIG. 2B). Using comparative cell ELISA and flow cytometry, it was determined that 90/1320 (6.8%) of phage antibodies selected on CaP cell line PC3 bound PC3 cells but not normal cells, including BPH-1, RWPE-1, MCF10A and HMEC (FIG. 2B-D, and Table 3). These phage antibodies were designated as 'highly' specific binders. By the same criteria, 30/360 (8.3%) and 25/270 (9.3%) of phage antibodies were highly specific for DU-145 and LNCaP prostate tumor cell lines respectively. The number of unique antibodies was determined by DNA fingerprinting and sequencing. Ninety unique antibodies were identified which were highly specific for CaP cell lines; 72 of these antibodies bound specifically to hormone refractory metastatic cell lines PC3 and DU-145. Most of these antibodies (70/72 total) bound to both the hormone refractory cell lines (FIG. 2C). Fifty out of 51 Du-145 binders cross-reacted with PC3 cells, while 20/21 PC3 binders cross-reacted with Du-145 cells. These results indicate that a large number of unique antibodies recognizing membrane antigens specific to prostate cancer cells were identified.'

TABLE 3

Summary of selection results on PC3, DU-145 (hormone-refractory), and LNCaP (hormone-sensitive) prostate cancer cell lines. Binding specificities were determined by whole-cell ELISA and flow cytometry. DNA fingerprinting and sequencing were used to identify the number of unique antibodies.

|  | PC3 | DU-145 | LNCap |
|---|---|---|---|
| Total Output (cfu$^a$) | $4 \times 10^6$ | $3 \times 10^6$ | $2 \times 10^6$ |
| Positive/Clones Screened | 255/1320 = 19.3% | 116/360 = 32.2% | 95/270 = 35.2% |
| Nonspecific binder | 67/1320 = 51/% | 35/360 = 9.7% | 24/270 = 8.8% |
| Binding to over-expressed marker | 137/1320 = 10.4% | 60/360 = 16.7% | 68/270 = 25.2% |
| Highly specific binder | 90/1320 = 6.8% | 30/360 = 8.3% | 25/270 = 9.3% |
| Unique Clones | 51/1320 = 3.9% | 21/360 = 5.8% | 21/270 = 7.8% |

To further confirm antibody specificity, the ability of phage antibodies to identify tumor cells in mixed cell populations was assessed using two color FACS. FITC-labeled normal cells were mixed with unlabeled prostate cancer cells and co-incubated with CaP-specific phage antibody. CaP-specific phage antibodies specifically stained prostate cancer cells but not normal cells in the mixed populations (FIG. 2D).

Selected Phage Antibodies Recognize Different Antigens than Existing Antibodies

Cell profiling experiments were performed using flow cytometry with CaP-specific phage antibodies in comparison with known antibodies that have been described as prostate- or prostate cancer-specific in the literature. The results are summarized in Table 4. The binding pattern of the selected CaP-specific phage antibodies are very different from that of known CaP antibodies, including anti-PSMA, anti-PSCA, anti-STEAP and anti-hepsin, and therefore likely recognize novel antigens or epitopes on the prostate cancer cell surface (Table 4). Phage antibody that exhibited the most specific binding patterns to both hormone refractory lines (PC3 and Du-145) were selected for further analysis.

TABLE 4

Summary of flow cytometry profiling of selected phage antibodies and known antibodies to prostate tumor antigens. Data were compiled from current studies and published data. Mean fluorescent intensity (MFI) per cell is indicated as: ++, strongly positive (sample/control > 100); +, positive (10 < sample/control < 100); +/−, weakly positive (5 < sample/control < 10); −/+, slightly positive (2 < sample/control < 5). PSMA, prostate specific membrane antigen; PSCA, prostate stem cell antigen; STEAP, six-transmembrane epithelial antigen of the prostate; PSGR, prostate-specific G protein coupled receptor.

|  | BPH-1 | RWPE-1 | LNCaP | PC3 | DU-145 | Ref |
|---|---|---|---|---|---|---|
| PSMA | + | +/− | + | − | − | This example and Fair et al. (1997) Prostate, 32: 140-148 and Reiter et al. (1998) Proc. Natl. Acad. Sci. USA, 95: 1735-1740 |

TABLE 4-continued

Summary of flow cytometry profiling of selected phage antibodies and known antibodies to prostate tumor antigens. Data were compiled from current studies and published data. Mean fluorescent intensity (MFI) per cell is indicated as: ++, strongly positive (sample/control > 100); +, positive (10 < sample/control < 100); +/−, weakly positive (5 < sample/control < 10); −/+, slightly positive (2 < sample/control < 5). PSMA, prostate specific membrane antigen; PSCA, prostate stem cell antigen; STEAP, six-transmembrane epithelial antigen of the prostate; PSGR, prostate-specific G protein coupled receptor.

| | BPH-1 | RWPE-1 | LNCaP | PC3 | DU-145 | Ref |
|---|---|---|---|---|---|---|
| PSCA | ND[a] | ND | − | − | − | This example and Hubert et al. (1999) Proc. Natl. Acad. Sci. USA, 96: 14523-14528 and Xu et al. (2000) Cancer Res., 60: 6568-6572 |
| STEAP | + | + | +/− | + | + | This example and Fair et al. (1997) Prostate, 32: 140-148 |
| PSGR | − | − | +/− | − | − | This example. |
| Hepsin | ND | ND | +/− | − | +/− | #[b] |
| A33 | − | − | − | ++ | ++ | # |
| M10A12 | − | − | − | ++ | ++ | # |
| M9E4 | − | − | ++ | ++ | ++ | # |
| Old A12 | − | − | − | ++ | ++ | # |
| M11G12 | − | −/+ | ++ | ++ | ++ | # |
| M11F12 | − | − | ++ | − | ++ | # |
| C10 | − | ++ | ++ | ++ | ++ | # |

[a]ND, not done
[b]#, this example.

Figure 3A:
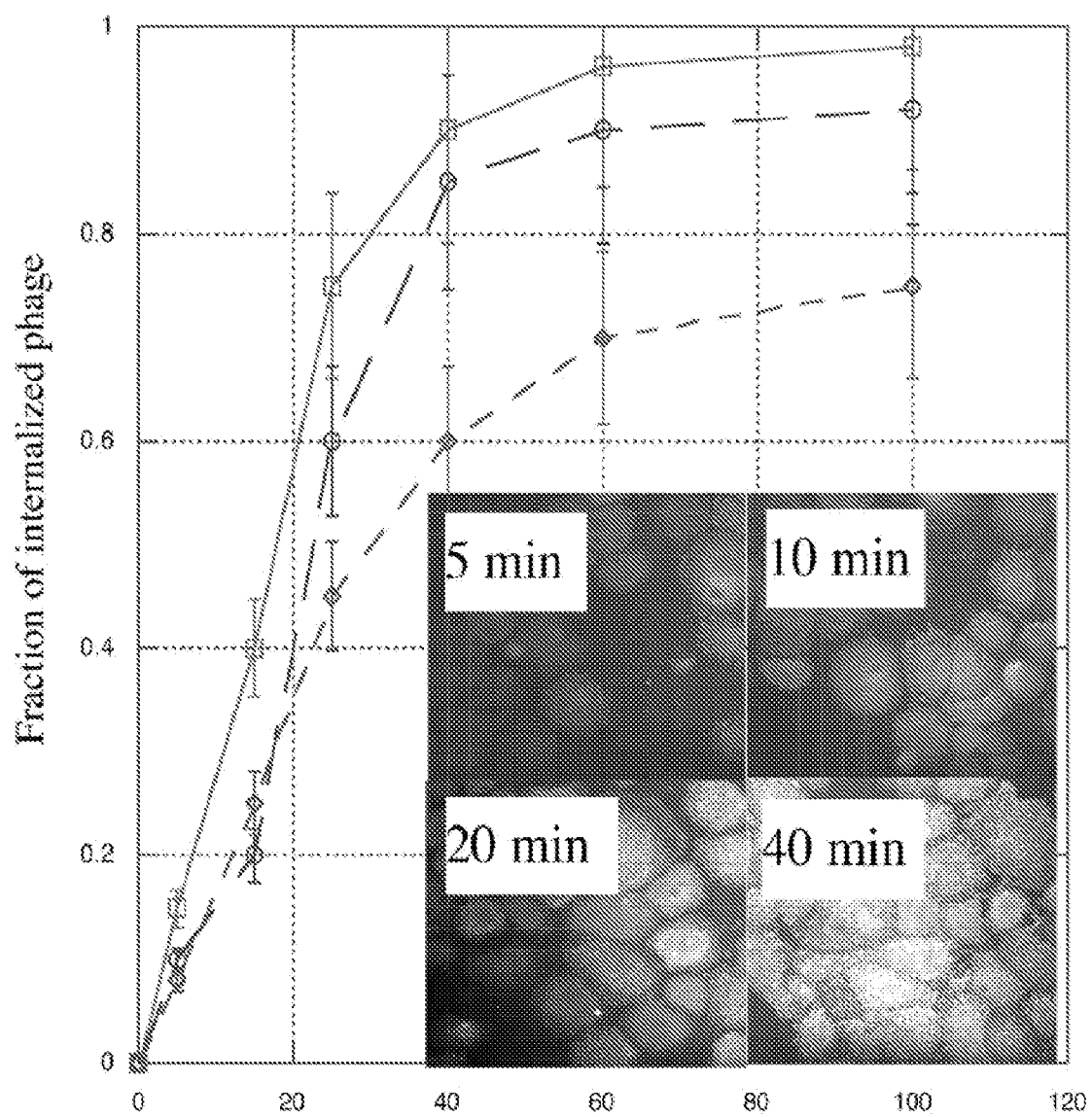
FIGS. 3A through 3C.
Figure 3B:
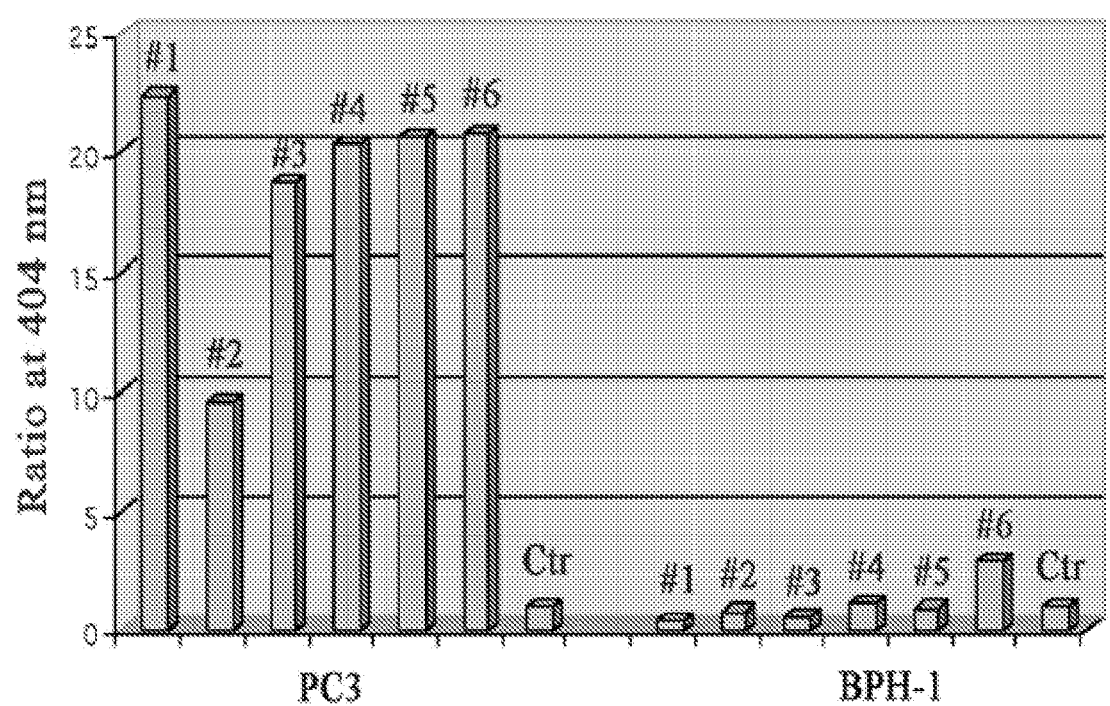
Figure 3C:
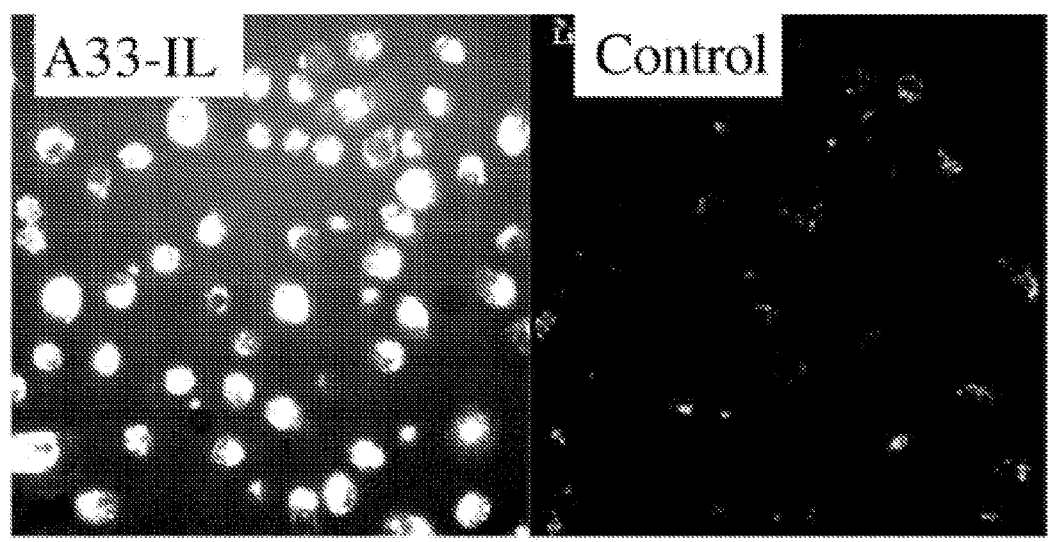

Selected Phage Antibodies are Rapidly Internalized and can be Used to Construct a Targeted Drug Delivery Vehicle:

Phage antibodies were isolated using a functional selection for triggering receptor endocytosis. To confirm that the selected antibodies possessed this phenotype and were endocytosed by CaP cells, the intracellular uptake of six unique phage antibodies was measured. All six phage antibodies were efficiently internalized by PC3 cells (FIG. 3A). This property of tumor-cell specific internalization can be exploited to create a generic approach for efficient tumor specific drug delivery. When attached to drug-encapsulated nanoparticles such as liposomes, CaP specific scFv are expected to deliver the liposomes to the tumor cytosol. To determine the utility of the CaP antibodies for intracellular drug delivery, we determined the quantitative uptake of immunoliposomes. Liposomes with surface bound CaP scFv were loaded with a pH sensitive fluorophore, pyranine (1-hydroxypyrene-3,6,8-trisulfonic acid, HPTS) (Nielsen et al. (2002) *Biochim Biophys Acta.*, 1591: 109-118) and intracellular uptake was determined by measurement of the pH-dependent fluorescence of HPTS, allowing quantification of scFv-HPTS-liposome in acidic endosomal compartments. Such immunoliposomes prepared from six different CaP specific scFv were efficiently endocytosed by PC3, with minimal uptake into BPH-1 cells (FIG. 3B). Without scFv, untargeted liposomes were not efficiently taken up by prostate cancer cells (FIG. 3C). These experiments demonstrate that scFv antibodies obtained via selection for internalization are capable of mediating targeted payload delivery. Those antibodies are candidates for the development of immunoliposome-based targeted prostate cancer therapeutics.

Figure 4:
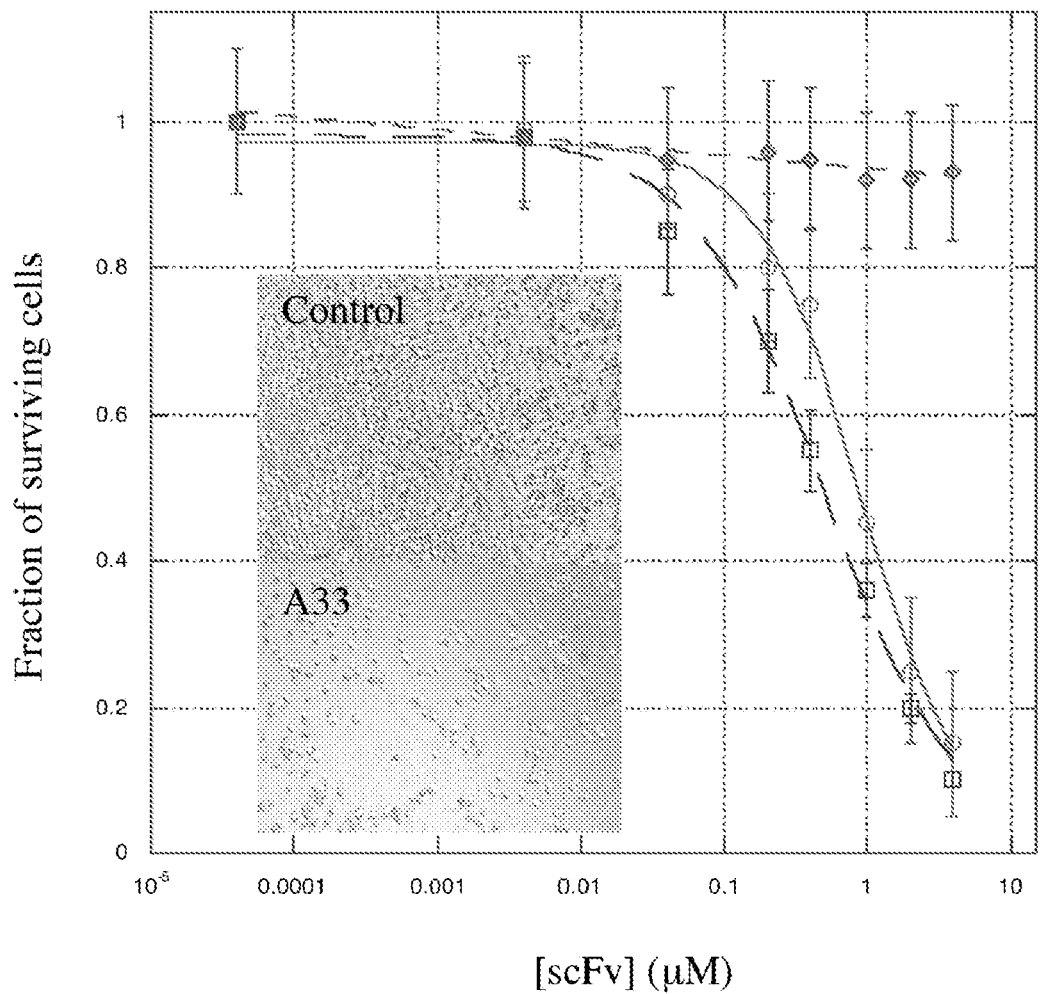
FIG. 4 shows the results of a cell proliferation assay. Purified scFv were incubated with PC3 cells. Circle: M9E4 scFv; Square: A33 scFv; Diamond: irrelevant, anti-hapten scFv. Insert: PC3 treated with PBS (control), and 1.8 µM A33.

Intrinsic Anti-Proliferative Activity of CaP Binding scFv:

It is likely that some of the surface molecules bound by internalizing CaP scFv are receptors, transporters or adhesion molecules that mediate important physiological processes of tumor cells. We thus hypothesized that a subset of the scFv might have intrinsic anti-proliferative activity. To test this hypothesis, the ability of CaP-specific internalizing scFv to inhibit CaP cell proliferation in vitro was assessed. PC3 and DU-145 cells were incubated with varying concentrations of highly purified, soluble native A33 or M9E4 scFv and cell proliferation was assessed by the tetrazolium salt MTT assay. Both scFv showed dose dependent growth inhibition, with $IC_{50}$ values between 0.5-1.8 μM, with a control scFv showing no inhibitory effect (FIG. 4). No inhibitory effect was observed on BPH-1 cells. These inhibitory scFv are candidates for the development of naked antibody based therapeutics.

Figure 5:
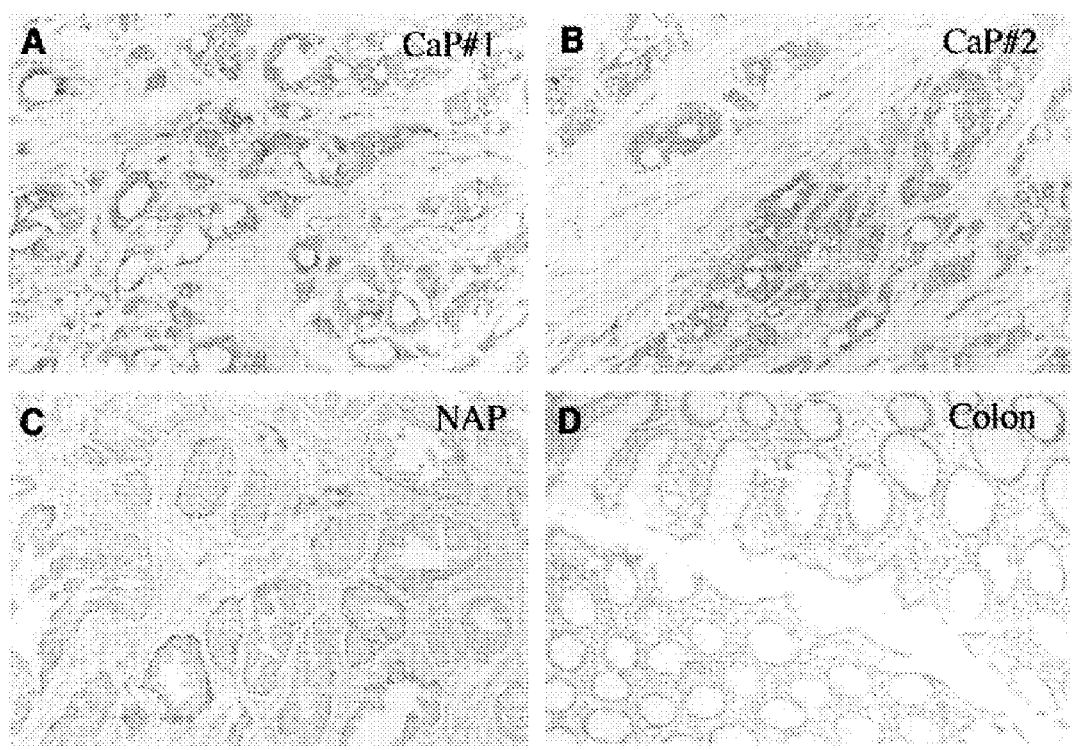
FIG. 5, panels A-C show immunohistochemistry studies of scFv binding to prostate cancer tissue. Frozen tissue sections were stained with A33 (scFv')$_2$ using HRP-DAB and the tissues counterstained with hematoxylin. (panel a) and (panel b) Staining on sections of prostate cancer Gleason scale 4+3 from two different patients (CaP #1 and CaP #2). (panel c) Staining on NAP, normal prostate tissue adjacent to prostate cancer. (panel d) Staining on normal colon epithelium. Magnification: 12.5×10.

Immunohistochemistry:

There is some controversy in the literature as to how well cell lines actually represent patient tumors, as cell lines may have undergone genetic and physiological changes during in vitro culture. To further address the relevance of the CaP-specific antibodies to human prostate cancer, immunohistochemical studies were performed on tissue sections from primary prostate tumor of high Gleason grades. FIG. 5 shows the staining results of the A33 (scFv')$_2$ dimer antibody on two different tissue specimens obtained from Gleason 3+4 patients (FIGS. 5A and B). There is intense staining of tumor epithelium, with minimal staining of normal adjacent prostate epithelium (FIG. 5C), normal breast epithelium (data not shown), or normal colon epithelium (FIG. 5D). A total of twenty high-grade prostate cancer patient samples have been examined, and positive A33 staining patterns were observed in 18/20 cases. A total of eight CaP-specific scFv antibodies have been subjected to immunohistochemistry studies on frozen tissue slides, six of which showed specific reactivity to prostate cancer epithelium. These experiments indicate that antibodies obtained from selection on tumor cell lines bind antigens that exist in patient samples and thus are clinically relevant to human prostate cancer. The corresponding antigens are overexpressed in prostate cancer and are likely targets for therapeutic intervention.

Materials and Methods.

Phage Display Library Construction and Preparation.

A multivalent fd phage display library consisting of 5×10$^8$ members was derived from a 7×10$^9$ member phagemid library (Sheets et al. (1998) *Proc Natl Acad Sci USA*, 95: 6157-6162) by subcloning the SfiI/NotI scFv insert from pHEN1 into bacterial vector fd-SfiI/NotI (O'Connell et al. (2002) *J Mol Biol*, 321: 49-56; Liu and Marks (2000) *Anal Biochem*, 286: 119-128; Huie et al. (2001) *Proc Natl Acad Sci USA.*, 98: 2682-2687). Phage were produced via growth in culture of *E. coli* TG1, concentrated by precipitation with polyethylene glycol (PEG) 8000, and purified by CsCl gradient centrifugation as previously reported (Id.).

Selection for Prostate Cancer Specific Internalizing Antibody.

Normal human fibroblasts, and non-cancerous epithelial lines RWPE-1, BPH-1, MCF10A and HMEC were used to deplete the phage library of nonspecific binders by incubating 10$^{12}$ phage particles with 10$^8$ cells for 4 hours at 4° C. Supernatant containing the depleted phage library was then incubated with 10$^6$ prostate cancer cells for 1 hour at 4° C. Cells were washed with cold PBS, and incubated with pre-warmed (37° C.) media/10% FCS at 37° C. for 30 min to allow receptor-mediated internalization. Non-internalized phage were removed by washing cells with glycine buffer (50 mM glycine, 150 mM NaCl, 200 mM urea, 2 mg/ml polyvinylpyrrolydone, pH 2.8) and by digesting cells with trypsin at 37° C. for 10 minutes. Cells were collected by centrifugation and lysed with 1 ml of 100 mM triethlyamine. Lysate was neutralized with 0.5 ml of 1 M Tris.HCl (pH 6.8), and was used to infect exponentially growing *E. coli* TG1 as previously described (Id.). The number of unique phage antibody was determined by patterns of BstNI digestion of scFv genes amplified by PCR from phage-infected bacteria (Liu et al. (2002) *J Mol. Biol.*, 315: 1063-1073). When restriction digestion patterns were ambiguous, scFv genes were sequenced to determine uniqueness.

Analysis of Phage Antibody Binding by Flow Cytometry.

$10^6$ cells were incubated with phage antibody ($5 \times 10^{11}$ cfu/ml) for one hour at 4° C. Bound phage were detected by using biotinylated anti-M13 antibody (Amersham-Pharmacia) and streptavidin-R-phycoerythrin (PE) or streptavidin-fluorescein isothiocyanate (FITC) (Molecular Probes). Cells were analyzed using a FACSort (Becton Dickinson). Mean fluorescence intensity (MFI) was calculated using CellQuest™ software (Becton Dickinson). For analysis of mixed cell populations by two color flow cytometry, the relevant normal cell line was pre-labeled with FITC labeling reagent, 6-(fluorescein-5-[and-6]-carboxamido)hexanoic acid, succinimidyl ester (5(6)-SFX, Molecular Probes) according to manufacture's instruction. Labeled and unlabeled cells were mixed and incubated with phage antibody at 4° C. for one hour. Bound phage were detected by biotinylated anti-fd rabbit polyclonal antibody (Sigma) and streptavidin-PE. For cytometry, the pre-labeled cell population was identified on the FL1 (FITC) channel, and the bound phage were detected on the FL2 (PE) channel, appropriately compensated. Experiments were performed with either cell population (normal vs. prostate cancer) labeled with similar results.

Expression and Purification of Prostate Cancer Specific Single Chain Fv Antibody.

The scFv gene was subcloned from the phage vector into the secretion vector pUC119mycHis, resulting in the addition of a c-myc epitope tag and hexahistidine tag at the C-terminus of the scFv. To create the (scFv')2 dimer (Adams et al. (1993) *Cancer Res*, 53: 4026-4034) for immunohistochemistry, the c-myc epitope tag was genetically removed from pUC119mycHis and a free cysteine was introduced at the C-terminus of the scFv preceding the hexahistidine tag. ScFv or (scFv')$_2$ dimmer were harvested from the bacterial periplasm and purified by immobilized metal affinity chromatography and gel filtration (Nielsen et al. (2002) *Biochim Biophys Acta.*, 1591: 109-118). Following purification of the (scFv')$_2$ dimmer protein, approximately 50% of scFv was in dimeric form as determined by non-reducing SDS-PAGE.

Immunohistochemistry.

Tissue sections from frozen and paraffin-embedded blocks were obtained from the Tissue Core of UCSF Comprehensive Cancer Center. For immunohistochemical analysis, tissue sections were incubated with purified dimeric scFv (50 µg/ml in 2% milk/PBS) at 4° C. for 4 hours, washed with PBS, incubated with a rabbit polyclonal anti-(His)$_6$ antibody diluted 1/400 (Santa Cruz Biotechnology), followed by biotinylated anti-rabbit antibody diluted 1/400 (Vector Lab) and HRP-conjugated streptavidin diluted 1/400 (Sigma). Binding was detected using DAB as the substrate (Sigma).

Growth Inhibition and Internalization Assays:

PC3 cells at 30% confluence were incubated with varying concentrations of affinity purified scFv at 37° C. for 72 hours in media containing 1% fetal calf serum. Growth status was assessed using the tetrazolium salt MTT assay (Promega), and IC50 was calculated using KaleidaGraph 3.5 (Synergy Software). For internalization assays, CaP-specific phage antibodies were biotinylated with sulfo-NHS-LC-biotin (Pierce), mixed with unlabeled helper phage M13K07 at the molar ratio of 1:100, and incubated with target cells at 37° C. for varying amount of time. Cells were washed with 100 mM glycine buffer, pH 2.8, fixed with 2% formaldehyde, permeabilized with ice cold 100% methanol, and incubated with streptavidin-FITC. The stained cells were first examined with an Axiophot fluorescence microscope (Zeiss), and further studied with a Leica TCS NT confocal laser fluorescence microscope (Leica).

Immunoliposome Preparation and Assay of Intracellular Delivery:

Liposomes were prepared from 1-palmitoyl-2-oleoyl-phosphatidylcholine (POPC), cholesterol, and methoxypoly (ethylene glycol (M.W. 2000)-distearoylphosphatidylethanolamine (PEG2000-DSPE) (3:2:0.3 molar ratio) (Avanti Polar Lipids) by lipid film hydration in a solution containing the pH-sensitive fluorophore HPTS, (1-hydroxypyrene-3,6,8-trisulfonic acid, pyranine), followed by extrusion through track-etched polycarbonate membranes with 100 nm pore size (Nielsen et al. (2002) *Biochim Biophys Acta.*, 1591: 109-118; Papahadjopoulos et al. (1991) *Proc Natl Acad Sci USA.*, 88: 11460-11464). A lipophilic derivative of Ni-NTA (Avanti Polar Lipids) was further inserted into the liposome to create a surface capable of capturing (his)$_6$-tagged scFv. To assess intracellular liposome delivery, HPTS liposomes (0.2 mM phospholipid) were added to cells along with 1 µg/ml of purified (his)$_6$ tagged scFv, incubated at 37° C. for 30 minutes and washed three times with saline containing 1 mM EDTA to remove cell surface-bound liposomes that failed to internalize. Uptake of scFv-HPTS immunoliposomes was determined by microfluorimetry with a Gemini microfluorometer (Molecular Devices) and by an inverted fluorescence microscope (Nikon).

Discussion:

Mapping Tumor Cell Surface Epitope Space by a Direct, Antibody Library-Based Approach.

Tumor-specific cell surface markers are invaluable for the development of targeted oncologic therapeutics due to their relatively easy accessibility to targeting molecules. Differential gene expression-based approaches have been widely employed for discovery and identification of these markers, but these approaches have significant limitations. First, the level of mRNA transcript production does not always correlate with that of protein expression (Watkins and Norbury (2002) *Br J Cancer*, 86: 1023-1027). Secondly, neither cDNA microarray nor other gene expression-based approaches can profile neoplastic changes in glycosylation or other post-translational modifications. Such changes have been shown to play an important role in tumor metastasis (Skubitz (2002) *Cancer Treat Res*, 107: 305-329) and may be critical determinants in modulating active anti-tumor immunity. Thus to analysis of the entire epitope space on the tumor cell surface alternative methodologies must be explored and developed.

For this work, a functional approach was taken to tumor-cell epitope mapping; specifically, we sought to identify tumor-specific epitopes not readily predicted or identified from microarray or other gene expression-based analyses. A large non-immune phage antibody library was constructed and selected directly on tumor cell surface to generate CaP-specific antibodies. The non-immune antibody library functions as an unbiased random shape repertoire potentially capable of recognizing any shape antigen on the tumor cell surface. Unbiased repertoires should provide more complete coverage of the tumor epitope space, compared to immunization and hybridoma technology, which typically yield multiple antibodies against a few dominant epitopes.

While phage libraries have been previously employed to identify tumor-specific antigens, the number of specific mAbs isolated has typically been small (Gao et al. (2003) *J Immunol Methods*, 274: 185-197; Poul et al. (2000) *J Mol Biol*, 301: 1149-1161; Cai and Garen (1995) *Proc Natl Acad Sci USA*, 92: 6537-6541; Li et al. (2001) *J Immunol*, 166: 432-438). Previously utilized antibody libraries were constructed in phagemid vectors which on average have only a single scFv molecule displayed on each phagemid particle. For this work, a multivalent antibody library was employed where 3-5 identical scFv molecules are displayed per phage. Multivalent display increases both the efficiency of depletion of non-specific antibodies and the positive selection of specific antibodies due to the increased binding from avidity effects of the multivalent phage antibody to target cell surface (Huie et al. (2001) *Proc Natl Acad Sci USA*., 98: 2682-2687; Liu et al. (2002) *J Mol. Biol.*, 315: 1063-1073). Moreover, the selection methodology was devised to isolate antibodies that trigger receptor-mediated endocytosis (Poul et al. (2000) *J Mol Biol*, 301: 1149-1161) and are thereby delivered directly into the tumor cell. This not only selects for antibodies with desirable biologic effects that can be exploited for intracellular drug delivery (Nielsen et al. (2002) *Biochim Biophys Acta.*, 1591: 109-118), but also leads to more efficient selection of phage libraries (Becerril et al. (1999) *Biochem Biophys Res Commun*, 255: 386-393). Since many receptors require dimerization or crosslinking for efficient internalization, the use of a multivalent phage display library increases the efficiency of phage internalization through receptor crosslinking (Id.). This allows more efficient recovery of phage antibody binding to more epitopes on more receptors and probably accounts for the much larger number of antibodies generated in this study, compared to the same antibody repertoire displayed monovalently and selected on breast tumor cells (Poul et al. (2000) *J Mol Biol*, 301: 1149-1161).

A Panel of Novel CaP-Specific Monoclonal Antibodies.

Direct cell selection yielded more than ninety phage antibodies that bind specifically to prostate cancer cells, including hormone refractory ones. Profiling by flow cytometry on a panel of normal and tumor cell lines reveals that the majority of CaP-specific antibodies display binding patterns different from those of known tumor antibodies, and therefore likely recognize novel cell surface antigens. Since only a few thousand clones were screened from the second round output of $5 \times 10^5$ antibodies, it is likely that a much larger number of tumor specific cell surface epitopes and antibodies remain to be identified. It is possible that phage antibody unique in sequences may nevertheless bind to the same epitope, effectively reducing the size of the tumor epitope space in our estimation. We have performed competition experiments with 15 unique phage antibodies by examining phage binding to target cells in the presence of soluble scFv of a different sequence. In all cases examined, there were no significant, dose-dependent competitions except when the phage antibody was co-incubated with soluble scFv of the same sequence (data not shown). Although this type of analysis has not been performed on all 93 CaP-specific phage antibodies, we conclude, based on the available data, that the majority of those antibodies recognize different epitopes. We have therefore not grossly overestimated the size and complexity of the tumor specific epitope space.

Our study points to a significant up-regulation of antigenic determinants on the surface of prostate cancer cells. This contrasts with previous studies using cDNA microarrays which suggest that a global transcriptional repression mediated by the polycomb gene EZH2 is the principal force driving prostate cancer development (Varambally et al. (2002) *Nature.*, 419: 624-629). Our results indicate that functional, proteome-based approaches provide complementary information on the immunochemical features characteristic of cancer cells which may not be revealed by gene expression-based studies.

Phage Antibodies are Efficiently Endocytosed.

All phage antibodies studied possessed the phenotype which the selections were designed to capture, the ability to trigger receptor mediated endocytosis. Purified native CaP-specific scFv were rapidly internalized into tumor cells and were capable of delivering nanoparticles (liposomes) specifically into prostate cancer cells. Drug-loaded immunoliposomes must be endocytosed for anti-tumor activity to provide both direct killing of tumor cells and bystander killing by diffusion of small molecule drugs to neighboring tumor cells (Park et al. (2002) *Clin Cancer Res.*, 8: 1172-1181). Immunoliposomes can be constructed from scFv (Nielsen et al. (2002) *Biochim Biophys Acta.*, 1591: 109-118) and can be designed to have a long circulating half-life and to be non-immunogenic (Papahadjopoulos et al. (1991) *Proc Natl Acad Sci USA.*, 88: 11460-11464). Other strategies can be designed to utilize internalizing antibody fragments for targeted tumor therapeutics. These applications include intracellular delivery of small molecule drugs via direct conjugation, cytotoxic gene fusions, immunotoxins, viral and non-viral gene delivery vehicles, and radionuclides (Carter (2001) *Nature Rev Cancer*, 1: 118-129).

Phage Antibodies have Intrinsic Anti-Tumor Activities.

A subset of CaP specific scFv had intrinsic anti-tumor activity, inhibiting proliferation of prostate cancer cells in vitro at sub-micromolar concentrations. This anti-tumor activity has not been typically observed with scFv isolated previously from cell selections of phage antibody libraries (Hoogenboom (2002) *Methods Mol Biol*, 178: 1-37). This direct anti-tumor activity may have resulted from selecting for antibodies which trigger internalization and which are likely to bind to biologically active receptors, transporters, or adhesion molecules which may play significant roles in tumor physiology. Such antigens, in effect, may not be merely byproducts of tumor transformation, but rather may play an integral role in this process. Based on this investigation, it appears that antibody endocytosis can be used as a surrogate marker for selection of antibodies with direct, intrinsic anti-tumor activity.

Clinical Relevance to Human Prostate Cancer.

A panel of more than 90 internalizing antibodies was generated which can be used therapeutically, either for intracellular drug delivery or as naked antibodies with direct anti-proliferative effects. These phage antibodies may also be useful diagnostically, and they may provide the means to identify novel tumor antigens which might be vaccine candidates or important new targets for the treatment of prostate cancer. Currently, few monoclonal antibodies exist which specifically recognize CaP cells, and fewer still are specific for hormone refractory cells. These include antibodies to a number of cell surface molecules including PSMA (Fair et al. (1997) *Prostate.* 32: 140-148), PSCA (Reiter et al. (1998) *Proc Natl Acad Sci USA.*, 95: 1735-1740), PSGR (Xu et al. (2000) *Cancer Res.*, 60: 6568-6572), STEAP (Hubert et al. (1999) *Proc Natl Acad Sci USA.*, 96: 14523-14528), and hepsin (Dhanasekaran et al. (2001) *Nature*, 412: 822-826). PSMA was isolated via murine immunization with membrane preparations of LNCaP cells. The other markers were identified during various studies of differential mRNA expression. Although originally considered to be prostate- or prostate cancer-specific, follow-up studies have found that expression of these markers in many cases is actually less restricted (Dhanasekaran et al. (2001) *Nature,* 412: 822-826; Reiter et al. (1998) *Proc Natl Acad Sci USA.,* 95: 1735-1740).

Phage selections were performed on established CaP cell lines. PC3 and DU-145 cells do not express PSA or androgen receptor, and exhibit androgen-independent growth. LNCaP cells, on the other hand, retain PSA and androgen receptor expression, and remain dependent on androgens. These diverse phenotypes were utilized as they may reflect distinct stages of prostate cancer development. It is possible that such cell lines cultured in vitro have undergone physiological and genetic changes and do not truly represent human prostate cancer in vivo. Tissue staining with CaP-specific single chain antibodies on frozen tissue was preformed to observe binding patterns in situ within tumors and identify those antibodies that are relevant to human prostate cancer. The results show that antibody obtained from cell line studies may be highly relevant clinically, consistent with previous observations (Cai and Garen (1996) *Proc Natl Acad Sci USA.,* 93: 6280-6285).

Several challenges remain to be addressed for the development of these antibodies in therapeutic applications. Foremost is the identification of the antigen bound by the antibodies. While we have been able to immunoprecipitate small amounts of antigen with some of the scFv, immunoprecipitation with high avidity IgG based on these scFv is the method of choice. Towards this objective, full length IgG are being constructed from the V-genes of six of the scFv with the most specific staining patterns by immunohistochemistry. IgG will be used for immunoprecipitation and the antigen bound can be readily identified by mass spectrometry. Construction of IgG will overcome two other scFv limitations: their use for in vivo studies of anti-tumor activity, which are precluded by the small size and rapid clearance of scFv and their limited use in immunohistochemistry. In the future, we anticipate utilization of the IgG will allow antigen identification, determination of its temporal and spatial pattern of expression, and determination of direct in vivo anti-tumor activity. Such data combined with in vivo studies of the drug delivery ability of the antibodies (Nielsen et al. (2002) *Biochim Biophys Acta.,* 1591: 109-118) should result in the identification of new antigens and targets for metastatic prostate cancer and the development of therapeutically useful antibodies for improved clinical strategies.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody or antigen-binding fragment thereof that specifically binds the antigen bound by the M10A12 single chain human antibody consisting of SEQ ID NO:23, wherein said isolated antibody or antigen-binding fragment thereof comprises a heavy chain variable (V$_H$) region comprising the 3 complementarity determining regions (CDRs) of the V$_H$ region of the amino acid sequence of SEQ ID NO:23 and a light chain variable region ($V_L$) comprising the 3 CDRs of the $V_L$ region of the amino acid sequence of SEQ ID NO:23.

2. The antibody of claim 1, wherein said antibody is a single chain antibody.

3. The antibody or antigen-binding fragment thereof of claim 1, wherein said antibody or antigen-binding fragment thereof is selected from the group consisting of an Fab, an (Fab')$_2$, an scFv, and an (ScFv')$_2$.

4. A chimeric molecule, said molecule comprising an effector attached to an antibody that specifically binds the antigen bound by the M10A12 single chain human antibody consisting of SEQ ID NO:23, said antibody comprising a $V_H$ comprising the 3 CDRs of the $V_H$ region of the amino acid sequence of SEQ ID NO:23 and a $V_L$ comprising the 3 CDRs of the $V_L$ region of the amino acid sequence of SEQ ID NO: 23.

5. The chimeric molecule of claim 4, wherein said effector is selected from the group consisting of an epitope tag, a second antibody, a label, a cytotoxin, a liposome, a radionuclide, a drug, a prodrug, a viral particle, a cytokine and a chelate.

6. The chimeric molecule of claim 4, wherein said effector is an epitope tag selected from the group consisting of an avidin and a biotin.

7. The chimeric molecule of claim 4, wherein said effector is a cytotoxin selected from the group consisting of a Diphtheria toxin, a Pseudomonas exotoxin, a ricin, an abrin and a thymidine kinase.

8. The chimeric molecule of claim 4, wherein said effector is a chelate comprising a metal isotope selected from the group consisting of $^{99}$Tc, $^{203}$Pb, $^{67}$Ga, $^{68}$Ga, $^{72}$As, $^{111}$In, $^{113m}$In $^{97}$Ru, $^{62}$Cu, $^{64}$Cu, $^{52}$Fe, $^{52m}$Mn $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$yb, $^{175}$Yb, $^{177}$Lu, $^{105}$Rh and $^{111}$Ag.

9. The chimeric molecule of claim 4, wherein said effector is a chelate comprising an alpha emitter.

10. The chimeric molecule of claim 9, wherein said alpha emitter is bismuth 213.

11. The chimeric molecule of claim 4, wherein said effector is a chelate comprising DOTA.

12. The chimeric molecule of claim 4, wherein said effector is a lipid or a liposome.

13. A pharmaceutical formulation, said formulation comprising: a pharmaceutically acceptable excipient and an antibody according to claim 1.

14. The pharmaceutical formulation of claim 13, wherein said formulation is a unit dosage formulation.

15. A pharmaceutical formulation said formulation comprising: a pharmaceutically acceptable excipient and a chimeric molecule according to claim 4.

16. The pharmaceutical formulation of claim 15, wherein said formulation is a unit dosage formulation.

17. A kit comprising a container containing an antibody of claim 1.

18. The kit of claim 17, further comprising an effector.

19. The kit of claim 18, wherein said effector comprises a chelate.

20. The kit of claim 17, wherein said antibody is in a pharmacologically acceptable excipient.

* * * * *